(12) United States Patent
Joseph

(10) Patent No.: US 8,093,383 B2
(45) Date of Patent: Jan. 10, 2012

(54) P70 S6 KINASE INHIBITORS

(75) Inventor: Sajan Joseph, Bangalore (IN)

(73) Assignee: Eli Lilly and Company, Indianapolis, IN (US)

( * ) Notice: Subject to any disclaimer, the term of this patent is extended or adjusted under 35 U.S.C. 154(b) by 308 days.

(21) Appl. No.: 12/396,103

(22) Filed: Mar. 2, 2009

(65) Prior Publication Data

US 2009/0163714 A1  Jun. 25, 2009

Related U.S. Application Data

(63) Continuation of application No. PCT/US2008/062143, filed on May 1, 2008.

(60) Provisional application No. 60/917,331, filed on May 11, 2007.

(51) Int. Cl.
C07D 487/00 (2006.01)

(52) U.S. Cl. ........................................................ 544/256

(58) Field of Classification Search .................. None
See application file for complete search history.

(56) References Cited

FOREIGN PATENT DOCUMENTS

| WO | WO 99/65909 A1 | 12/1999 |
|---|---|---|
| WO | WO 2005/117909 | 12/2005 |
| WO | WO 2006/046024 | 5/2006 |
| WO | WO 2006/071819 | 7/2006 |
| WO | WO 2007/003960 | 1/2007 |
| WO | WO 2007/125310 | 11/2007 |
| WO | WO 2007/125321 | 11/2007 |
| WO | WO 2008/012635 | 1/2008 |
| WO | WO 2008/075109 | 6/2008 |

*Primary Examiner* — Jeffrey Murray

(74) *Attorney, Agent, or Firm* — Tina M. Tucker; Danica Hostettler

(57) ABSTRACT

The present invention provides p70 S6 kinase inhibitors of the formula:

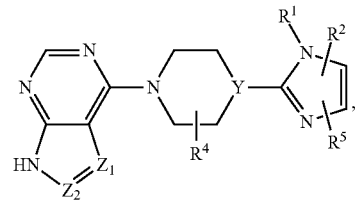

pharmaceutical formulations comprising them, and methods for their use.

3 Claims, No Drawings

P70 S6 KINASE INHIBITORS

This application is a 35 U.S.C. 120 Continuation Application of PCT/US2008/062143 filed May 1, 2008, which claims priority to U.S. Provisional Application No. 60/917,331, filed May 11, 2007.

BACKGROUND OF THE INVENTION p70 S6 kinase is a downstream effector of the phosphatidylinositol 3 kinase (PI3K)/AKT/mammalian target of rapamycin (mTOR) signaling pathway and p70 S6 kinase is commonly activated in many human solid tumors. p70 S6 kinase activity regulates ribosome biogenesis, cell growth, and cell cycle progression in response to mitogenic stimulation. As such, suppressing p70 S6 kinase activity will block ribosome biogenesis, synthesis of select proteins, cell growth, and cell cycle progression. Thus a role for p70 S6 kinase exists in tumor cell proliferation and protection of cells from apoptosis. Furthermore, inhibitors of p70 S6 kinase are described as useful in treating infections, inflammation and tumor formation, as well as metabolic diseases and disorders. (WO 2005/117909, WO 2006/071819, WO 2006/046024, WO 2007/125321 and WO 2008/012635). The present invention provides surprisingly potent compounds that inhibit p70 S6 kinase activity. In addition particular compounds of the present invention are highly bioavailable.

BRIEF SUMMARY OF THE INVENTION

The present invention provides compounds of Formula I:

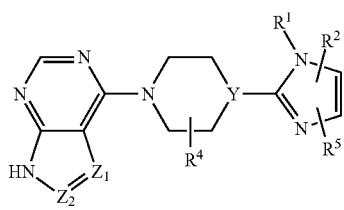

I where:
Y is N or $CR^6$;
$Z_1$ and $Z_2$ are independently $CR^3$ or N, provided that $Z_1$ and $Z_2$ are not both N;
$R^1$ is H or $C_1$-$C_4$ alkyl;
$R^2$ is phenyl optionally substituted with a first substituent selected from $C_1$-$C_4$ alkyloxy, cyano, $NO_2$, halo, trifluoromethyl, and trifluoromethoxy and optionally further substituted with a second substituent selected from the group consisting of halo;
$R^3$ is hydrogen, halo, $C_1$-$C_4$ alkyl, $C_3$-$C_6$ cycloalkyl, or $C_2$-$C_6$ alkynyl, wherein $C_2$-$C_6$ alkynyl is optionally substituted with hydroxy;
$R^4$ and $R^5$ are independently hydrogen or $C_1$-$C_4$ alkyl;
$R^6$ is hydrogen or hydroxy; or a pharmaceutically acceptable salt thereof.

This invention also provides compounds of Formula I wherein:
Y is N or $CR^6$;
$Z_1$ and $Z_2$ are independently $CR^3$ or N, provided that $Z_1$ and $Z_2$ are not both N;
$R^1$ is H or $C_1$-$C_4$ alkyl;
$R^2$ is phenyl optionally substituted with a first substituent selected from $C_1$-$C_4$ alkyloxy, cyano, $NO_2$, halo, trifluoromethyl, and trifluoromethoxy and optionally further substituted with a second substituent selected from the group consisting of halo;
$R^3$ is hydrogen, halo, or $C_3$-$C_6$ cycloalkyl;
$R^4$ and $R^5$ are independently hydrogen or $C_1$-$C_4$ alkyl;
$R^6$ is hydrogen or hydroxy; or a pharmaceutically acceptable salt thereof.

The present invention also provides a method of inhibiting p70 S6 kinase in a mammal comprising administering to a mammal in need of such treatment an effective amount of a compound of Formula I or IA or a pharmaceutically acceptable salt thereof.

The present invention also provides a method of inhibiting angiogenesis in a mammal comprising administering to a mammal in need of such treatment an effective amount of a compound of Formula I or a pharmaceutically acceptable salt thereof.

Additionally, the present invention also provides a method of treating adenocarcinomas of the colon in a mammal comprising administering to a mammal in need of such treatment an effective amount of a compound of Formula I or a pharmaceutically acceptable salt thereof.

Additionally, the present invention also provides a method of treating non-small-cell lung cancer in a mammal comprising administering to a mammal in need of such treatment an effective amount of a compound of Formula I or a pharmaceutically acceptable salt thereof.

The present invention also provides a method of treating glioblastoma multiforme in a mammal comprising administering to a mammal in need of such treatment an effective amount of a compound of Formula I or a pharmaceutically acceptable salt thereof.

The present invention further provides a method of treating ovarian carcinoma in a mammal comprising administering to a mammal in need of such treatment an effective amount of a compound of Formula I or a pharmaceutically acceptable salt thereof.

The present invention further provides a method of treating leukemia in a mammal comprising administering to a mammal in need of such treatment an effective amount of a compound of Formula I or a pharmaceutically acceptable salt thereof.

The present invention further provides a method of treating pancreatic carcinoma in a mammal comprising administering to a mammal in need of such treatment an effective amount of a compound of Formula I or a pharmaceutically acceptable salt thereof.

The present invention additionally provides a method of treating prostate cancer in a mammal comprising administering to a mammal in need of such treatment an effective amount of a compound of Formula I or a pharmaceutically acceptable salt thereof.

The present invention further provides a method of treating mammary carcinoma in a mammal comprising administering to a mammal in need of such treatment an effective amount of a compound of Formula I or a pharmaceutically acceptable salt thereof.

The present invention also provides a method of treating lymphangioleiomyomatosis in a mammal comprising administering to a mammal in need of such treatment an effective amount of a compound of Formula I or a pharmaceutically acceptable salt thereof.

The invention also provides a pharmaceutical formulation comprising a compound of Formula I or a pharmaceutically acceptable salt thereof, in combination with a pharmaceutically acceptable carrier, diluent, or excipient.

This invention also provides the use of a compound of Formula I or IA or a pharmaceutically acceptable salt thereof for the manufacture of a medicament for the inhibition of p70 S6 kinase. Additionally, this invention provides a compound of Formula I or a pharmaceutically acceptable salt thereof for use in inhibition of p70 S6 kinase in mammals. Furthermore, this invention provides a pharmaceutical composition adapted for the inhibition of p70 S6 kinase comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the inhibition of angiogenesis. Additionally, this invention provides a compound of Formula I or a pharmaceutically acceptable salt thereof for use in inhibition of angiogenesis in mammals. Furthermore, this invention provides a pharmaceutical composition adapted for the inhibition of angiogenesis comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of adenocarcinomas of the colon. Additionally, this invention provides a compound of Formula I or a pharmaceutically acceptable salt thereof for use in treatment of adenocarcinomas of the colon in mammals. Furthermore, this invention provides a pharmaceutical composition adapted for the treatment of adenocarcinomas of the colon comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the treatment of non-small-cell lung cancer. Additionally, this invention provides a compound of Formula I or a pharmaceutically acceptable salt thereof for use in treatment of non-small-cell lung cancer in mammals. Furthermore, this invention provides a pharmaceutical composition adapted for the treatment of non-small-cell lung cancer comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of glioblastoma multiforme. Additionally, this invention provides a compound of Formula I or a pharmaceutically acceptable salt thereof for use in treatment of glioblastoma multiforme in mammals. Furthermore, this invention provides a pharmaceutical composition adapted for the treatment of glioblastoma multiforme comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of ovarian carcinoma. Additionally, this invention provides a compound of Formula I or a pharmaceutically acceptable salt thereof for use in treatment of ovarian carcinoma in mammals. Furthermore, this invention provides a pharmaceutical composition adapted for the treatment of ovarian carcinoma comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of leukemia. Additionally, this invention provides a compound of Formula I or a pharmaceutically acceptable salt thereof for use in treatment of leukemia in mammals. Furthermore, this invention provides a pharmaceutical composition adapted for the treatment of leukemia comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of pancreatic carcinoma. Additionally, this invention provides a compound of Formula I or a pharmaceutically acceptable salt thereof for use in treatment of pancreatic carcinoma in mammals. Furthermore, this invention provides a pharmaceutical composition adapted for the treatment of pancreatic carcinoma comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of prostate cancer. Additionally, this invention provides a compound of Formula I or a pharmaceutically acceptable salt thereof for use in treatment of prostate cancer in mammals. Furthermore, this invention provides a pharmaceutical composition adapted for the treatment of prostate cancer comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of mammary carcinoma. Additionally, this invention provides a compound of Formula I or a pharmaceutically acceptable salt thereof for use in treatment of mammary carcinoma in mammals. Furthermore, this invention provides a pharmaceutical composition adapted for the treatment of mammary carcinoma comprising a compound of Formula I or a pharmaceutically acceptable salt thereof in combination with one or more pharmaceutically acceptable excipients, carriers, or diluents thereof.

This invention further provides the use of a compound of Formula I or a pharmaceutically acceptable salt thereof for the manufacture of a medicament for the treatment of lymphangioleiomyomatosis. Additionally, this invention provides a compound of Formula I or a pharmaceutically acceptable salt thereof for use in treatment of lymphangioleiomyomatosis in mammals. Furthermore, this invention provides a pharmaceutical composition adapted for the treatment of lymphangioleiomyomatosis comprising a compound of Formula I or a pharmaceutically acceptable salt thereof in combination with one or more pharmaceutically acceptable excipients, carriers, or diluents thereof.

In addition, the invention provides for the use of a compound of Formula I in therapy.

DETAILED DESCRIPTION OF THE INVENTION

The general chemical terms used in the formulae above have their usual meanings. For example, the term "$C_1$-$C_4$ alkyl" refers to a straight or branched, monovalent, saturated aliphatic chain of one to four carbon atoms, for example, methyl, ethyl, propyl, isopropyl, butyl, isobutyl, and t-butyl and the like. Likewise, the term "$C_1$-$C_3$ alkyl" includes methyl, ethyl, and isopropyl and the like.

As used herein the term "$C_1$-$C_4$ alkoxy" refers to a straight or branched alkyl chain having from one to four carbon atoms attached to an oxygen atom. Typical $C_1$-$C_4$ alkoxy groups include methoxy, ethoxy, propoxy, isopropoxy, butoxy, tert-butoxy and the like.

As used herein, the terms "Halo" refer to a chlorine, bromine, iodine, or fluorine atom, unless otherwise specified herein.

As used herein the term "$C_3$-$C_6$ cycloalkyl" means a fully saturated ring comprising carbon and hydrogen atoms and includes cyclopropyl and cyclobutyl.

As used herein, the term "$C_2$-$C_6$ alkynyl" is a straight or branched alkynyl chain having from two to six carbon atoms and one triple bond, including, but not limited to, ethynyl, propynyl, butynyl, pentynyl, and the like.

Compounds of this invention are bases, and accordingly react with any of a number of organic and inorganic acids to form pharmaceutically acceptable salts and the present invention includes the pharmaceutically acceptable salts of the compounds of Formula I or IA. The term "pharmaceutically acceptable salt" as used herein, refers to salts of the compounds of Formula I that are substantially non-toxic to living organisms. Such salts include the pharmaceutically acceptable salts listed in Journal of Pharmaceutical Science, 66, 2-19 (1977), which are known to the skilled artisan. Hydrochloride, mesylate, and tosylate (also known as p-toluene sulfonate) salts are preferred salts. The hydrochloride and tosylate salts are most preferred.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention. The specific stereoisomers and enantiomers of compounds of Formula I can be prepared by one of ordinary skill in the art utilizing well known techniques and processes, such as those disclosed by J. Jacques, et al., "Enantiomers, Racemates, and Resolutions", John Wiley and Sons, Inc., 1981, and E. L. Eliel and S. H. Wilen, "Stereochemistry of Organic Compounds", (Wiley-Interscience 1994), and European Patent Application No. EP-A-838448, published Apr. 29, 1998. Examples of resolutions include recrystallization techniques or chiral chromatography.

The skilled artisan will also appreciate that compounds of Formula I where $R^1$ is hydrogen or where $Z_1$ or $Z_2$ are N exist as tautomers. Although tautomers are structurally distinct, the skilled artisan will appreciate that they exist in equilibrium and are easily and rapidly interconvertible under ordinary conditions. (See, March, *Advanced Organic Chemistry*, Third Edition, Wiley Interscience, New York, N.Y. (1985), pages 66-70; and Allinger, *Organic Chemistry*, Second Edition, Worth Publishers, New York, N.Y., (1976), page 173). As such, the representation of a compound of Formula I in a single tautomeric form contemplates both tautomeric forms individually and mixtures thereof. Likewise, the naming of a compound of Formula I where, for example, $R^1$ is hydrogen either as 1H-imidazole or a 3H-imidazole contemplates both tautomeric forms.

Certain classes of compounds of Formula I are preferred p70 S6 kinase inhibitors. The following paragraphs describe such preferred classes:
 a) Y is $CR^6$;
 b) Y is CH;
 c) $R^1$ is H;
 d) $R^1$ is $CH_3$;
 e) $Z_1$ is $CR^3$;
 f) $Z_1$ is CH;
 g) $Z_2$ is N;
 h) $R^2$ is phenyl substituted with a first substituent selected from the group consisting of halo and trifluoromethyl, and optionally further substituted with a second substituent which is halo;
 i) $R^2$ is phenyl substituted with a first substituent selected from halo and trifluoromethyl and further substituted with a second substituent which is halo;
 j) $R^2$ is phenyl substituted in the 3 or 4 position with a first substituent selected from the group consisting of halo and trifluoromethyl, and optionally further substituted with a second substituent which is halo.
 k) $R^2$ is phenyl substituted in the 3 or 4 position with a first substituent selected from the group consisting of halo and trifluoromethyl, and further substituted with a second substituent which is halo.
 l) $R^2$ is phenyl substituted in the 3 position with a first substituent selected from the group consisting of halo and trifluoromethyl, and optionally further substituted in the 4 position with a second substituent which is halo;
 m) $R^5$ is H;
 n) The compound of Formula I is a free base;
 o) The compound of Formula I is a salt;
 p) The compound of Formula I is the hydrochloride salt;
 q) The compound of Formula I is the tosylate salt.

Other preferred compounds of Formula I are those where Y is $CR^6$ and $R^1$ is H or $CH_3$. Additional preferred compounds of Formula I are those where Y is $CR^6$ and $R^1$ is H or $CH_3$; and $R^2$ is phenyl substituted with a first substituent selected from the group consisting of halo and trifluoromethyl, and optionally further substituted with a second substituent which is halo.

Preferred compounds of Formula I also include those where Y is $CR^6$ and $R^1$ is H or $CH_3$; $R^2$ is phenyl substituted with a first substituent selected from the group consisting of halo and trifluoromethyl, and optionally further substituted with a second substituent which is halo; $R^5$ is H; $Z_1$ is $CR^3$ and $Z_2$ is N.

Also preferred are those compounds of Formula I in which Y is CH; $R^1$ is H or $CH_3$; $R^2$ is phenyl substituted with a first substituent selected from the group consisting of halo and trifluoromethyl, and optionally further substituted with a second substituent which is halo; $R^5$ is H; $Z_1$ is CH; and $Z_2$ is N.

In addition, preferred are those compounds of Formula I in which Y is CH; $R^1$ is H or $CH_3$; $R^2$ is phenyl substituted with a first substituent selected from the group consisting of halo and trifluoromethyl, and further substituted with a second substituent which is halo; $R^5$ is H; $Z_1$ is CH; and $Z_2$ is N.

More preferred compounds of Formula I are those in which Y is CH; $R^1$ is H or $CH_3$; $R^2$ is phenyl substituted in the 3 position with a first substituent selected from the group consisting of halo and trifluoromethyl, and optionally further substituted in the 4 position with a second substituent which is halo; $R^5$ is H; $Z_1$ is CH; and $Z_2$ is N.

In addition, more preferred compounds of Formula I are those in which Y is CH; $R^1$ is H or $CH_3$; $R^2$ is phenyl substituted in the 3 position with a first substituent selected from the group consisting of halo and trifluoromethyl, and further substituted in the 4 position with a second substituent which is halo; $R^5$ is H; $Z_1$ is CH; and $Z_2$ is N.

Particularly preferred are those compounds of Formula I in which Y is CH, $Z_1$ is CH and $Z_2$ in N.

The following compound, 4-{4-[4-(3-(Trifluoromethyl)-phenyl)-1H-imidazol-2-yl]-piperidin-1-yl}-1H-pyrazolo[3,4-d]pyrimidine:

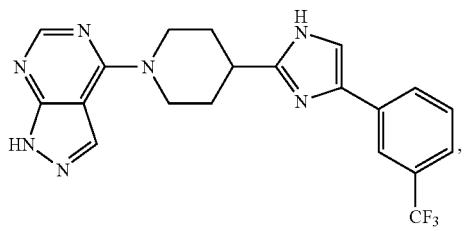

or a pharmaceutically acceptable salt therefore, is most especially preferred.

Additionally, the compound 4-{4-[4-(4-Fluoro-3-trifluoromethyl-phenyl)-1-methyl-1H-imidazol-2-yl]-piperidin-1-yl}-1H-pyrazolo[3,4-d]pyrimidine:

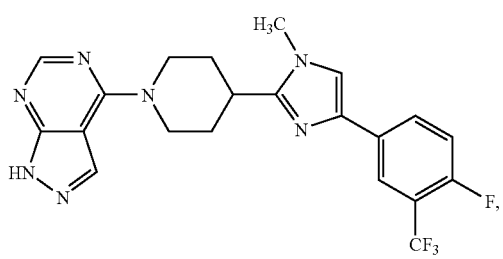

or a pharmaceutically acceptable salt thereof, is also most especially preferred.

The compounds of Formula I are inhibitors of p70 S6 kinase and are therefore useful in the treatment of metabolic diseases and disorders such as obesity, diabetes, metabolic syndrome, insulin resistance, hyperglycemia, hyperaminoacidemia, and hyperlipidemia, and proliferative disorders, particularly glioblastoma multiforme, colorectal cancer, hepatocellular cancer, lung cancer, breast cancer, ovarian cancer, and renal cell carcinoma in mammals. In addition, it has been found that the p70 S6 kinase pathway is activated in cells of benign tumors, such as those associated with lymphangioleiomyomatosis (LAM). See Journal of Bological Chemistry, 277:34, 30958-30967 (2002), and Modern Pathology 19, 839-846 (2006). Thus p70 S6 kinase inhibitors may also be useful in treating LAM. Inhibitors of p70 S6 kinase are also useful inhibitors of angiogenesis in mammals. It is preferred that the mammal to be treated is a human.

The compounds of Formula I can be prepared by one of ordinary skill in the art following art recognized techniques and procedures. More specifically, compounds of Formula I can be prepared as set forth in the schemes, methods, and examples set forth below. It will be recognized by one of skill in the art that the individual steps in the following schemes may be varied to provide the compounds of Formula I or IA. The reagents and starting materials are readily available to one of ordinary skill in the art. All substituents, unless otherwise specified, are as previously defined. Some substituents have been eliminated in the following schemes for the sake of clarity and are not intended to limit the teaching of the schemes in any way.

Compounds of Formula I may be prepared as illustrated in the following scheme where $R^1$, $R^2$, $R^4$, $R^5$, $Z_1$, $Z_2$ and Y are as previously defined, and L is a suitable leaving group such as halo.

SCHEME 1

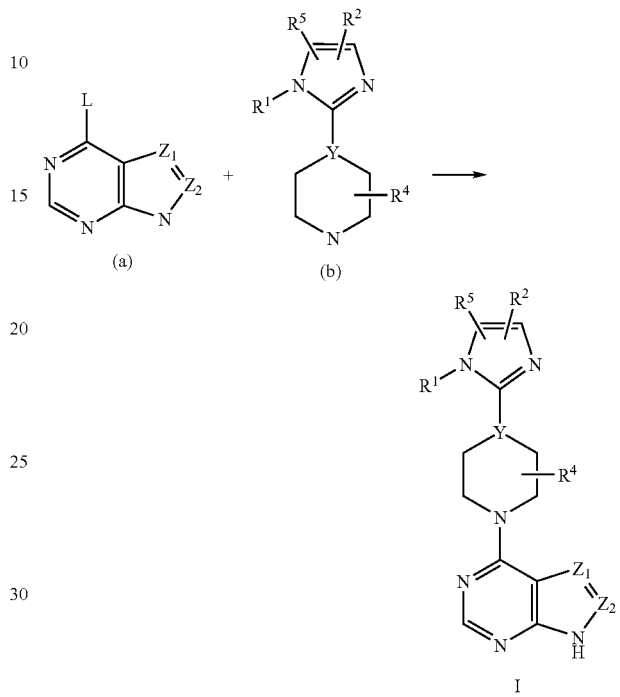

A substituted pyrazolopyrimidine (or purine or pyrrolopyrimidine) compound of formula (a) is reacted with a substituted piperazine or piperidine of formula (b) to form compounds of Formula I or IA. For example, a solution of a compound of formula (a), the piperazine (b) and a suitable base such as triethylamine, diisopropylethylamine, or N-methylmorpholine, in a suitable solvent, such as propanol or isopropyl alcohol are heated to about 70° C.-100° C. to provide compounds of Formula I or IA, which may then be isolated and, if necessary and desired, purified using techniques well known in the art, such as chromatography.

Compounds of formula (a) are commercially available, or may be synthesized by methods known to the skilled artisan. For example, compounds of formula (a) where $Z_1$ is $CR^3$ and $Z_2$ is N may be prepared from allopurinol by reaction with a chlorinating agent such as phosphoryl chloride and heating to about 80° C.-90° C. Further, compounds of formula (a) may be substituted if desired under conditions well known in the art. For example, a compound of formula (a) where $Z_1$ or $Z_2$ is $CR^3$ is fluorinated upon exposure an appropriate fluorinating agent, such as [1-(chloromethyl)-4-fluoro-1,4-diazonibicyclo[2.2.2]octanebis(tetrafluoroborate)] in a suitable solvent or mixture of suitable solvents, such as acetonitrile and acetic acid. Moreover, compounds of formula (a) where $R^3$ is alkyl or cycloalkyl are synthesized by methods known in the art. For instance, dichloropyrimidine is reacted with cyclopropane carbaldehyde in the presence of strong base such as LDA, in a solvent such as THF, at cooled temperatures to produce the requisite alcohol. Oxidation in the presence of chromium (VI) oxide at 0° C. in a suitable solvent such as acetone provides the required ketone, which is then reacted with hydrazine hydrate in a suitable solvent such as THF at room temperature to provide clycloalkyl-substituted pyrazolopyrimidine compounds of formula (a). Additionally, methods of producing compounds where $R^3$ is alkynyl are known to the skilled artisan. For example, a chlorinated compound of formula (a) trimethylsilylacetylene in triethylamine and a suitable solvent such as DMF and/or THF using tetrakis (triphenylphosphine)palladium(0) $(Pd(Ph_3P)_4)$ as a catalyst to afford the ethynylsubstituted compound of formula (a).

The requisite piperidine/piperazine compounds (b) may be prepared as illustrated in the following scheme, where $R^1$, $R^2$, $R^4$, $R^5$ and Y are as previously described, and PG is a suitable protecting group.

nium acetate or ammonium chloride in a sealed vessel, or for compounds where $R^5$ is H, upon exposure to microwave heat under pressure. Alternatively, compounds of formula (b1) may be formed by reacting amidine (e) with an appropriate halo ketone in a suitable solvent, such as DMF or acetone, in the presence of a base, such as potassium carbonate or sodium carbonate, followed by deprotection under conditions well-known to the skilled artisan. Hydroxypiperidines of formula (b1) may also synthesized by reacting a phenacyl bromide of formula (m) with formamide in the presence of heat. The imidazole (n) is then added to a suitable solvent such as THF, cooled, and treated with a nitrogen protecting group such as

SCHEME 2

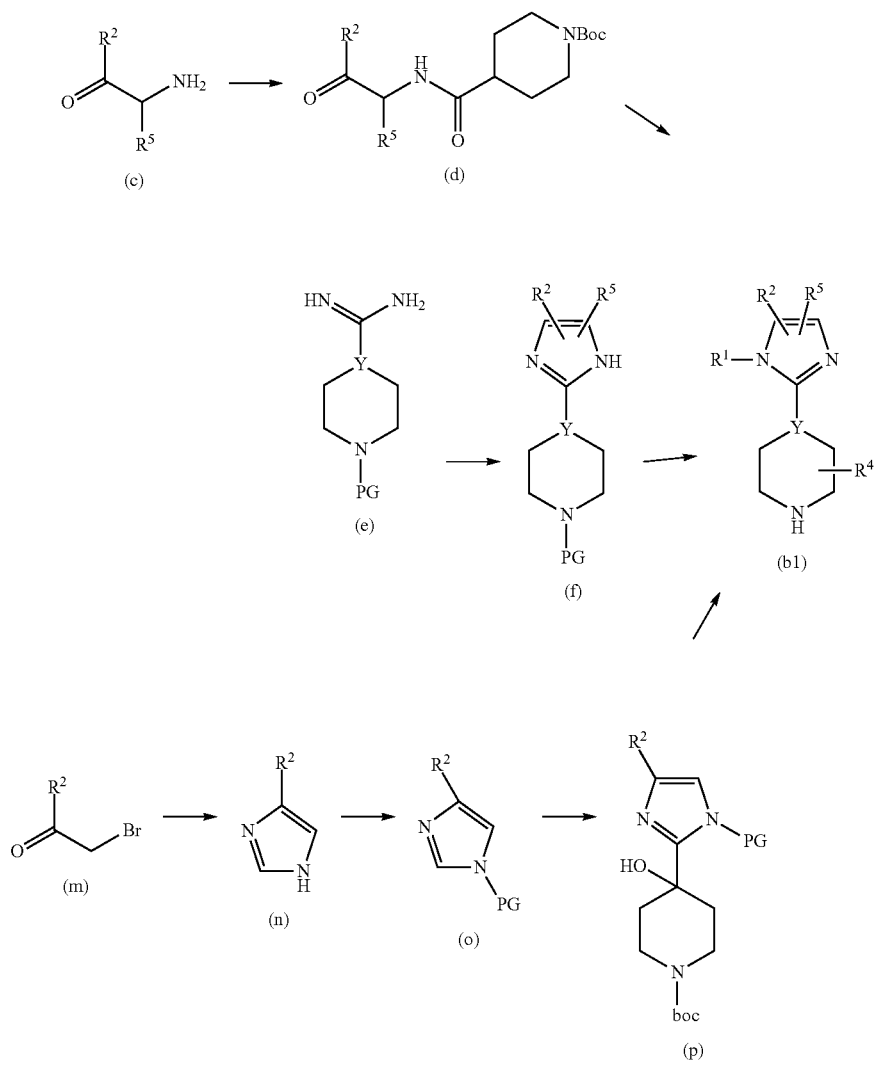

Amine (c) is reacted with a protected piperidine in the presence of suitable coupling agents such as isobutyl chloroformate, 1-ethyl-3-[3-dimethylaminopropyl]-carbodiimide hydrochloride (EDC), or 1-propanephosphonic acid cyclic anhydride (PPA) and an appropriate base such as N-methylmorpholine or triethylamine, in a suitable solvent such as THF, methylene chloride, or N,N-dimethylformamide (DMF) at reduced temperatures to form amide compounds of formula (d). The subsequent imidazole piperidine (b1), where Y is $CR^6$ is formed upon exposure of compound (d) to ammo- 2,2-(trimethylsilyl)ethoxy-methyl chloride in the presence of sodium hydride while allowing the reaction mixture to warm to room temperature to provide the intermediate of formula (O). The subsequent protected imidazole may then be treated with a metalating agent, such as n-butyllithium, in an inert solvent, such at THF, under reduced temperatures and under an inert atmosphere. This mixture is treated with an appropriately substituted piperidinone and allowed to warm to room temperature for about 1 h to give compounds of type (p).

Treatment of intermediate (p) with an aqueous acid such as 1 N HCl at elevated temperatures gives (b1).

The required amidines may be synthesized as described in scheme 3, wherein PG is a suitable protecting group:

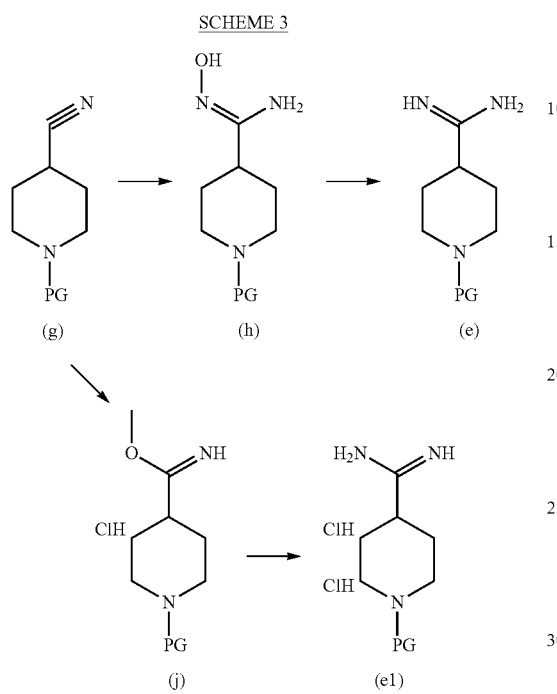

Amidine (e) is readily produced from nitrites. More specifically, hydroxylamine hydrochloride dissolved in a suitable solvent, such as water, is reacted with cyanopiperidine (g) in the presence of a base such as sodium carbonate in a suitable solvent, such as in methanol and exposed to heat to provide the hydroxycarbamimidoyl-piperidine (h). The hydroxycarbamimidoylpiperidine (h) in a suitable solvent, such as acetic acid, is then hydrogenated via palladium catalyst in the presence of acetic acid anhydride under pressure to provide amidine (e).

Alternatively, a carboximidic acid (j) is formed by dissolving cyanopiperidine (g) in a suitable solvent such as methanol, cooling, then reacting with hydrogen chloride gas. The amidine is then produced by treating carboximidic acid (j) with ammonia in methanol, then saturating the mixture with ammonia gas.

The skilled artisan will appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will also appreciate that the protecting groups may be removed at any convenient point in the synthesis of the compounds of the present invention. Methods for introducing and removing nitrogen protecting groups are well known in the art; see, for example, Greene and Wuts, *Protective Groups in Organic Synthesis,* 3rd Ed., John Wiley and Sons, New York, Chapter 7 (1999). Furthermore, the skilled artisan will appreciate than in many circumstances, the order in which moieties are introduced is not critical. The particular order of steps required to produce the compounds of Formula I is dependent upon the particular compound being synthesized, the starting compound and the relative lability of the substituted moieties.

The abbreviations, symbols and terms used in the examples and assays have the following meanings: BuOH=butanol, DCM=dichloromethane, DMF=N,N-dimethylformamide, EtOAc=ethyl acetate, EtOH=ethanol, MeOH=methanol, Pd(OH)$_2$/C=palladium hydroxide on carbon (Pearlman's catalyst), h=hour(s), LDA=lithium diisopropylamide, EDCI=1-(3-dimethylaminopropyl)-3-ethylcarbodiimide hydrochloride, Et$_2$O=diethyl ether, Et$_3$N (or TEA)=triethylamine, NaBH(OAc)$_3$=sodium triacetoxyborohydride, TBAF=tetrabutyl ammonium fluoride, Tf$_2$O=trifluoromethanesulfonic anhydride, THF=tetrahydrofuran.

Preparation 1

2-Bromo-1-(2-fluoro-5-trifluoromethyl-phenyl)-propan-1-one

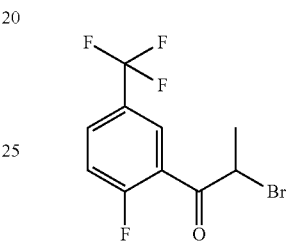

Slowly add a solution of bromine (3.34 g, 0.95 equiv) in dichloromethane (80.00 mL) to a solution of 2-fluoro-5-(trifluoromethyl)propiophenone (5 g, 22.03 mmol) in dichloromethane (80 mL) is with stirring so that the brown color of bromine just disappears. Wash the reaction mixture with saturated NaHCO$_3$, dry over Na$_2$SO$_4$ and concentrate to provide 6.22 g of crude material.

MS(ES): m/z=301.2 [M+2H].

The compounds of Preparations 2-5-D may be prepared essentially as described in Preparation 1.

| Preparation | Compound | MS (ES): m/z [M + 2H] |
|---|---|---|
| 2 | 2-Bromo-1-(4-fluoro-3-trifluoromethyl-phenyl)-propan-1-one | 301.2 |
| 3 | 2-Bromo-1-(2-chloro-5-trifluoromethyl-phenyl)-ethanone | 285.2 |
| 4 | 2-Bromo-1-(3-fluoro-5-trifluoromethyl-phenyl)-ethanone | 287.2 |
| 5 | 2-Bromo-1-(2-fluoro-5-trifluoromethyl-phenyl)-ethanone | 287.2 |
| 5-A | 2-Bromo-1-(4-trifluoromethyl-phenyl)-propan-1-one | 281 |
| 5-B | 2-Bromo-1-(3-trifluoromethyl-phenyl)-propan-1-one | 281.2 |
| 5-C | 2-Bromo-1-(3-chloro-4-fluorophenyl)-propan-1-one | 265.2 |
| 5-D | 2-Bromo-1-(3-fluorophenyl)-propan-1-one | 231.2 |

Preparation 6

2-Amino-1-(3-(trifluoromethyl)phenyl)ethanone hydrochloride

Add 3-(trifluoromethyl)phenacyl bromide (10 g, 37.4 mmol) to a solution of hexamethylenetetramine (HMTA) (5.80 g, 41.3 mmol) in carbon tetrachloride (100 mL). Stir at room temperature overnight. Filter the precipitate and suspend the filter cake in ethanol (200 mL). Dilute the mixture with concentrated hydrochloric acid (28 mL), and stir the mixture at room temperature overnight. Filter the precipitate, and concentrate the filtrate in vacuo to provide an off-white solid. Recrystallize the solids from hot 1% concentrated hydrochloric acid in 2-propanol taking care not to cool below room temperature to provide 2-amino-1-(3-(trifluoromethyl)phenyl)ethanone hydrochloride (7.67 g, 86%).

MS(APCI): m/z=204 [M+H].

The compounds of Preparations 7-16 may be prepared essentially as described in Preparation 6.

| Preparation | Compound | Physical Data |
|---|---|---|
| 7 | 2-Amino-1-(4-(trifluoromethyl)-phenyl)ethanone hydrochloride | MS (APCI): m/z = 204 [M + H] |
| 8 | 2-Amino-1-phenylethanone hydrochloride (titurated from hot propanol) | $^1$H NMR (500 MHz, DMSO-$d_6$) δ8.80-8.10 (br s, 3H), 8.02 (dd, J = 1.0, 8.5 Hz, 2H), 7.75-7.72 (m, 1H), 7.61-7.58 (m, 2H), 4.59 (s, 2H) |
| 9 | 2-Amino-1-(4-chlorophenyl)ethanone hydrochloride | $^1$H NMR (DMSO-$d_6$) δ 8.05-8.02 (m, 2H), 7.69-7.66 (m, 2H), 4.59 (s, 2H) |
| 10 | 2-Amino-1-(4-fluoro-3-(trifluoromethyl)phenyl)ethanone hydrochloride | $^1$H NMR (DMSO-$d_6$) δ 8.44-8.35 (m, 2H), 7.98-7.80 (m, 1H), 5.11-4.90 (m, 2H), 4.73-4.68 (m, 2H) |
| 11 | 2-Amino-1-(3-fluoro-4-(trifluoromethyl)phenyl)ethanone hydrochloride | $^1$H NMR (DMSO-$d_6$) δ 8.55-8.40 (br s, 2H), 8.15 (d, J = 18 Hz, 2H), 7.98-7.80 (m, 1H), 5.11-4.90 (m, 2H), 4.73-4.68 (m, 2H) |
| 12 | 2-Amino-1-(3-fluoro-5-trifluoromethyl-phenyl)-ethanone hydrochloride | $^1$H NMR (DMSO-$d_6$, 400 MHz): δ: 3.93 (2H, s), 7.41 (1H, d, J = 8.8 Hz), 8.10 (1H, s), 8.16 (1H, s), 8.18 (3H, s). |
| 13 | 2-Amino-1-(2-chloro-5-trifluoromethyl-phenyl)-ethanone hydrochloride | MS (ES): m/z = 238.2 [M + H] |
| 14 | 2-Amino-1-(2-fluoro-5-trifluoromethyl-phenyl)-ethanone hydrochloride | MS (ES): m/z = 222.2 [M + H] |
| 15 | 3-(2-Amino-acetyl)-benzonitrile hydrochloride | $^1$H NMR (DMSO-$d_6$, 400 MHz): δ: 4.62 (2H, s), 7.81-7.77 (1H, m), 8.18 (1H, d, J = 7.6 Hz), 8.28 (1H, d, J = 8.4 Hz), 8.50 (1H, s), 8.56 (3H, s). |
| 16 | 4-(2-Amino-acetyl)-benzonitrile hydrochloride | $^1$H NMR (DMSO-$d_6$, 400 MHz): δ: 4.62 (2H, s), 8.06 (2H, d, J = 8.4 Hz), 8.16 (2H, d, J = 8.4 Hz), 8.54 (3H, s). |

Preparation 17

2-Amino-1-(3-(trifluoromethoxy)phenyl)ethanone

Add sodium azide (583 mg, 8.96 mmol) to a solution of 3-(trifluoromethoxy)-phenacyl bromide (2.17 g, 7.66 mmol) in methanol (20 mL). Stir at room temperature for 2 h. Concentrate the mixture in vacuo. Dissolve the residue in EtOAc (20 mL) and wash with water (10 mL). Dry the organic layer (Na$_2$SO$_4$), filter, and concentrate filtrate in vacuo to provide 2-azido-1-(3-(trifluoromethoxy)phenyl)ethanone (1.70 g, 91%). $^1$H-NMR (CDCl$_3$): δ7.83 (m, 1H), 7.77 (s, 1H), 7.56 (m, 1H), 7.49 (m, 1H), 4.55 (s, 2H).

Add palladium on carbon (720 mg, 10% Pd/C, 50% water by weight) to a nitrogen purged solution of 2-azido-1-(3-(trifluoromethoxy)phenyl)ethanone (1.70 g, 6.93 mmol) in ethanol (15 mL). Purge the flask with hydrogen (balloon). Stir at room temperature overnight. Filter the mixture over Celite®, rinse the Celite® with ethanol (3×30 mL), and concentrate the filtrate in vacuo to provide crude 2-amino-1-(3-(trifluoromethoxy)phenyl)ethanone (1.56 g, 88%). $^1$H NMR (DMSO-$d_6$) δ 8.56 (br s, 2H), 8.07 (m, 1H), 7.95 (s, 1H), 7.76 (m, 2H), 4.63 (s, 2H).

Preparation 18

2-Amino-1-(4-fluoro-3-trifluoromethyl-phenyl)-propan-1-one toluene-4-sulfonic acid salt Add sodium azide (640.94 mg; 1.05 equiv; 9.76 mmoles) in one portion to a solution of 2-Bromo-1-(4-fluoro-3-trifluoromethyl-phenyl)-propan-1-one (2.78 g; 1.00 equiv; 9.30 mmoles) in tetrahydrofuran (15 mL). Stir the mixture at room temperature overnight. Filter the solids and wash with THF. Add the crude azide (1.00 equiv; 9.30 mmoles; 2.43 g) to a solution of triphenylphosphine (1.06 equiv; 9.86 mmoles; 2.61 g) and p-Toluenesulfonic Acid (2.2 equiv; 20.47 mmoles; 3.56 g) in tetrahydrofuran (15 mL) under 20° C. Stir the mixture overnight. Filter the solid, then wash with THF to obtain 920 mg (24%) of the title compound.

MS(ES): m/z=236.2 [M+H].

The compounds of Preparations 18A to 18-D may be prepared essentially as described in Preparation 18.

| Preparation | Compound | MS (ES): m/z [M + H] |
|---|---|---|
| 18-A | 2-Amino-1-(4-trifluoromethylphenyl)-propan-1-one toluene-4-sulfonic acid salt | 217.2 |
| 18-B | 2-Amino-1-(3-trifluoromethylphenyl)-propan-1-one toluene-4-sulfonic acid salt | 217 |

| Preparation | Compound | MS (ES): m/z [M + H] |
|---|---|---|
| 18-C | 2-Amino-1-(3-chloro-4-fluorophenyl)-propan-1-one toluene-4-sulfonic acid salt | 210 |
| 18-D | 2-Amino-1-(3-fluorophenyl)-propan-1-one toluene-4-sulfonic acid salt | 167 |

Preparation 19 tert-Butyl 4-(2-oxo-2-(3-(trifluoromethyl)phenyl)ethylcarbamoyl)piperidine-1-carboxylate

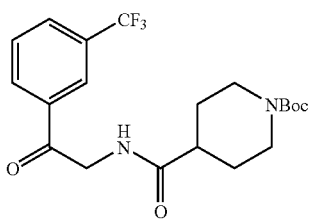

Add N-methylmorpholine (13.0 mL, 118 mmol) to a solution of 1-(tert-butoxycarbonyl)piperidine-4-carboxylic acid (11.2 g, 48.8 mmol) in THF (400 mL) at −10° C. and stir for 5 min. Add isobutyl chloroformate (5.1 mL, 38.8 mmol) and continue stirring at −10° C. for 2 h. Add 2-amino-1-(3-(trifluoromethyl)phenyl)ethanone hydrochloride (9.35 g, 39.0 mmol) and continue stirring for 1 h. Add methylene chloride (500 mL) to the mixture and filter. Wash the filtrate with sat. aqueous sodium bicarbonate (400 mL) and concentrate in vacuo. Purify the residue by silica gel chromatography (330 g RediSep column, eluting with a gradient of 0% to 100% ethyl acetate:hexane, 6.0 L) to provide tert-butyl 4-(2-oxo-2-(3-(trifluoromethyl)phenyl)ethylcarbamoyl)piperidine-1-carboxylate (9.72 g, 60%).

MS (APCI): m/z=315 $[M-C_5H_8O_2+H]^+$.

The compounds of Preparations 20-25 may be prepared essentially as described in Preparation 19.

Preparation 26 tert-Butyl 4-(2-oxo-2-(3-(trifluoromethoxy)phenyl)ethylcarbamoyl)piperidine-1-carboxylate Add triethylamine (1.1 mL, 7.89 mmol) and 1-(3-dimethylaminopropyl)-3-ethylcarbodiimide hydrochloride (EDC) (1.51 g, 7.87 mmol) to a solution of 2-amino-1-(3-(trifluoromethoxy)phenyl)ethanone (1.56 g, 6.10 mmol) and 1-(tert-butoxycarbonyl)piperidine-4-carboxylic acid (1.66 g, 7.24 mmol) in $CH_2Cl_2$ (15 mL) at 0° C. Stir at 0° C. for 3 h, then at room temperature overnight. Concentrate the mixture in vacuo. Purify the residue by silica gel chromatography (80 g $SiO_2$ eluting with 50% ethyl acetate/hexanes, 1 L) to provide tert-butyl 4-(2-oxo-2-(3-(trifluoromethoxy)phenyl)ethylcarbamoyl)piperidine-1-carboxylate (1.50 g, 57%).

MS (APCI): m/z=331 $[M-C_5H_8O_2+H]^+$.

Preparation 27

4-[2-(4-Fluoro-3-trifluoromethyl-phenyl)-1-methyl-2-oxo-ethylcarbamoyl]-piperidine-1-carboxylic acid tert-butyl ester Add dimethylformamide (20 mL) is to a mixture of 2-amino-1-(4-fluoro-3-trifluoromethyl-phenyl)-propan-1-one toluene-4-sulfonic acid salt (900 mg; 1.00 equiv; 2.21 mmoles) and 1-Boc-piperidine-4-carboxylic acid (Boc-Inp-OH) (613.96 mg, 1.20 equiv; 2.65 mmoles) at room temperature. Add N-methylmorpholine (6.00 equiv; 13.26 mmoles; 1.46 mL) to the above solution, then 1-propanephosphonic acid cyclic anhydride (1.50 equiv; 3.31 mmoles; 862.14 μL) at 0° C. Warm the mixture to room temperature while stirring for one hour. Dilute the mixture with EtOAc, wash with water, 1M citric acid, water, saturated $NaHCO_3$, and saturated aqueous sodium chloride and dry over $Na_2SO_4$. Purify the residue by dissolving in $CH_2Cl_2$, loading onto a silica gel column and eluting with EtOAc to give 500 mg (51%) of the title compound.

MS(ES): m/z=445.2 [M−H].

The compounds of Preparations 28-32 may be prepared essentially as described in Preparation 27.

| Preparation | Compound | Physical Data MS (APCI) |
|---|---|---|
| 20 | tert-Butyl 4-(2-oxo-2-(4-(trifluoromethyl)phenyl)-ethylcarbamoyl)piperidine-1-carboxylate | m/z = 315 $[M - C_5H_8O_2 + H]^+$ |
| 21 | tert-Butyl 4-(2-oxo-2-phenylethylcarbamoyl)-piperidine-1-carboxylate | m/z = 247 $[M - C_5H_8O_2 + H]^+$ |
| 22 | tert-Butyl 4-(2-(4-chlorophenyl)-2-oxoethylcarbamoyl)piperidine-1-carboxylate | m/z = 280 $[M - C_5H_8O_2 + H]^+$ |
| 23 | tert-Butyl 4-(2-(2,4-dichlorophenyl)-2-oxoethylcarbamoyl)piperidine-1-carboxylate | m/z = 315 $[M - C_5H_8O_2 + H]^+$ |
| 24 | tert-Butyl 4-(2-(4-fluoro-3-(trifluoromethyl)phenyl)-2-oxoethylcarbamoyl)piperidine-1-carboxylate | m/z = 433 [M + H] |
| 25 | tert-Butyl 4-(2-(3-fluoro-4-(trifluoromethyl)phenyl)-2-oxoethylcarbamoyl)piperidine-1-carboxylate | m/z = 433 [M + H] |

| Preparation | Compound | MS (ES) |
|---|---|---|
| 28 | 4-[2-(4-Cyano-phenyl)-2-oxo-ethylcarbamoyl]-piperidine-1-carboxylic acid tert-butyl ester | m/z = 372 [M$^+$ + H] |
| 29 | 4-[2-(3-Cyano-phenyl)-2-oxo-ethylcarbamoyl]-piperidine-1-carboxylic acid tert-butyl ester | m/z = 372 [M$^+$ + H] |
| 30 | 4-[2-(2-Chloro-5-trifluoromethyl-phenyl)-2-oxo-ethylcarbamoyl]-piperidine-1-carboxylic acid tert-butyl ester | m/z = 449 [M$^+$ + H] |
| 31 | 4-[2-(3-Fluoro-5-trifluoromethyl-phenyl)-2-oxo-ethylcarbamoyl]-piperidine-1-carboxylic acid tert-butyl ester | m/z = 433 [M$^+$ + H] |
| 32 | 4-[2-(2-Fluoro-5-trifluoromethyl-phenyl)-2-oxo-ethylcarbamoyl]-piperidine-1-carboxylic acid tert-butyl ester | m/z = 433 [M$^+$ + H] |
| 32-A | Tert-butyl 4-(1-oxo-1-(4-(trifluoromethyl)phenyl)propan-2-ylcarbamoyl]-piperidine-1-carboxylate | m/z = 428.2 [M$^+$ + H] |
| 32-B | Tert-butyl 4-(1-oxo-1-(3-(trifluoromethyl)phenyl)propan-2-ylcarbamoyl]-piperidine-1-carboxylate | m/z = 428 [M$^+$ + H] |
| 32-C | Tert-butyl 4-(1-oxo-1-(3-chloro-4-fluorophenyl)propan-2-ylcarbamoyl]-piperidine-1-carboxylate | m/z = 412 [M$^+$ + H] |
| 32-D | Tert-butyl 4-(1-oxo-1-(3-fluorophenyl)propan-2-ylcarbamoyl]-piperidine-1-carboxylate | m/z = 378 [M$^+$ + H] |

Preparation 33

4-(4-(3-(Trifluoromethyl)phenyl)-1H-imidazol-2-yl)piperidine

Microwave heat a mixture of tert-butyl 4-(2-oxo-2-(3-(trifluoromethyl)phenyl)-ethylcarbamoyl)piperidine-1-carboxylate (2.5 g, 6.09 mmol) and NH$_4$Cl (1.68 g, 31.4 mmol) in ethanol (20 mL) at 300 W, 120° C., and 200 PSI for 16 h in a CEM Discover microwave apparatus. Cool the mixture to room temperature. Repeat the procedure with a second portion of tert-butyl 4-(2-oxo-2-(3-(trifluoromethyl)phenyl)ethylcarbamoyl)-piperidine-1-carboxylate (2.35 g, 5.67 mmol) and NH$_4$Cl (1.8 g, 33.6 mmol) in ethanol (20 mL) utilizing the same microwave and heating program. Cool the mixture to room temperature. Repeat the above procedure with a third portion of tert-butyl 4-(2-oxo-2-(3-(trifluoromethyl)phenyl)ethylcarbamoyl)piperidine-1-carboxylate (2.0 g, 4.82 mmol) and NH$_4$Cl (1.34 mg, 25.0 mmol) in ethanol (15 mL) at 300 W, 160° C., and 200 PSI for 12 h in a microwave apparatus. Cool the mixture to room temperature. Combine the batches, adsorb onto silica gel, and concentrate in vacuo. Purify the residue by silica gel chromatography (120 g RediSep column, eluting with a gradient of 0% through 100% CMA:methylene chloride, 3 L) to provide 4-(4-(3-(trifluoromethyl)phenyl)-1H-imidazol-2-yl)piperidine (3.40 g, 75%).

MS (APCI): m/z=296 [M+H].

The compounds of Preparations 34-35 may be prepared essentially as described in Preparation 33.

| Preparation | Compound | Physical Data |
|---|---|---|
| 34 | 4-(4-(4-(Trifluoromethyl)phenyl)-1H-imidazol-2-yl)piperidine | MS (APCI): m/z = 296 [M + H] |
| 35 | 4-(4-(2,4-Dichlorophenyl)-1H-imidazol-2-yl)piperidine | MS (ES): m/z = 296 [M + H] |

Preparation 36

4-(4-Phenyl-1H-imidazol-2-yl)piperidine hydrochloride

Microwave heat a mixture of tert-butyl 4-(2-oxo-2-phenyl-ethylcarbamoyl)-piperidine-1-carboxylate (1.0 g, 2.88 mmol) and NH$_4$Cl (0.462 g, 8.65 mmol) in ethanol (12 mL) at 300 W, 160° C., and 14 bar for 11 h in a Personal Chemistry microwave. Cool the mixture to room temperature, add silica gel (5 mL), and concentrate the mixture in vacuo. Purify the residue by silica gel chromatography (80 g RediSep column, elute with a gradient of 0% through 100% CMA/methylene chloride over 60 min, 60 mL/min) to provide 4-(4-phenyl-1H-imidazol-2-yl)piperidine (0.418 g, 64%) as an off-white solid. Add 4-(4-phenyl-1H-imidazol-2-yl)piperidine (0.060 g, 0.26 mmol) to methylene chloride (15 mL) and concentrated hydrochloric acid (28 μL). Stir the mixture for 45 min, then concentrate the mixture in vacuo to provide 4-(4-phenyl-1H-imidazol-2-yl)piperidine hydrochloride (0.070 g, 99%).

MS (APCI): m/z=228 [M+H].

The compound of Preparation 37 may be prepared essentially as described in Preparation 36.

| Preparation | Compound | Physical Data |
|---|---|---|
| 37 | 4-(4-(4-Chlorophenyl)-1H-imidazol-2-yl)piperidine hydrochloride | MS (APCI): m/z = 262 [M + H] |

Preparation 38

4-(4-(4-Fluoro-3-(trifluoromethyl)phenyl)-1H-imidazol-2-yl)piperidine hydrochloride Microwave heat a mixture of tert-butyl 4-(2-oxo-2-(4-(trifluoromethyl)phenyl)-ethylcarbamoyl)piperidine-1-carboxylate (1.7 g, 3.92 mmol) and NH$_4$Cl (0.579 g, 10.8 mmol) in ethanol (17 mL) at 300 W, 120° C., and 14 bar for 12 h in a Personal Chemistry microwave. Cool the mixture to room temperature and add silica gel (20 g). Purify the residue by silica gel chromatography (330 g RediSep column, elute with a gradient of 0% to 100% CMA/methylene chloride over 30 min and hold at 100% CMA for an additional 30 min, 100 mL/min) to provide 4-(4-(4-fluoro-3-(trifluoromethyl)phenyl)-1H-imidazol-2-yl)piperidine (600 mg, 51%). MS (APCI): m/z=314 [M+H].

Suspend 4-(4-(4-fluoro-3-(trifluoromethyl)phenyl)-1H-imidazol-2-yl)piperidine (250 mg, 0.80 mmol) in methanol (20 mL) and add hydrogen chloride (2 M in diethyl ether, 0.798 mL, 0.80 mmol). Stir at room temperature for 30 min. Concentrate the mixture in vacuo, and add water (15 mL) and acetonitrile (5 mL). Freeze-dry the mixture to afford an off-white solid. Dry the solid in vacuo at 100° C. for 2 h to afford 4-(4-(4-fluoro-3-(trifluoromethyl)phenyl)-1H-imidazol-2-yl)piperidine hydrochloride as an off-white solid (220 mg, 79%).

MS (APCI): m/z=314 [M+H].

Preparation 39

4-(4-(3-Fluoro-4-(trifluoromethyl)phenyl)-1H-imidazol-2-yl)piperidine hydrochloride Microwave heat a mixture of tert-butyl 4-(2-(3-fluoro-4-(trifluoromethyl)phenyl)-2-oxoethylcarbamoyl)piperidine-1-carboxylate (517 mg, 1.19 mmol) and NH$_4$Cl (350 mg, 6.54 mmol) in ethanol (2 mL) at 300 W, 120° C., and 200 PSI with power max on for 12 h in a CEM Discover microwave. Cool the mixture to room temperature and add silica gel (~5 g). Purify the residue by silica gel chromatography (40 g RediSep column, elute with a gradient of 0% through 100% CMA/methylene chloride over 60 min, 40 mL/min) to provide 4-(4-(4-fluoro-3-(trifluoromethyl)phenyl)-1H-imidazol-2-yl)piperidine (228 mg, 61%) as an off-white solid. MS (APCI): m/z=314 [M+H].

Dissolve the product (29 mg) in methanol (2 mL) and add hydrogen chloride (2 M in diethyl ether, 95 µL) and stir at room temperature for 30 min. Concentrated the mixture in vacuo, add water (10 mL), and freeze-dry to afford 4-(4-(3-fluoro-4-(trifluoromethyl)phenyl)-1H-imidazol-2-yl)piperidine hydrochloride (29 mg) as an off-white solid.

MS (APCI): m/z=314 [M+H].

Preparation 40

4-(4-(3-(Trifluoromethoxy)phenyl)-1H-imidazol-2-yl)piperidine

Add tert-butyl 4-(2-oxo-2-(3-(trifluoromethoxy)phenyl)ethylcarbamoyl)-piperidine-1-carboxylate (1.50 g, 3.48 mmol) to a mixture of ammonium acetate (1.40 g, 18.1 mmol), and glacial acetic acid (10 mL) and heat at reflux for 15 h. Cool the mixture to room temperature and concentrated in vacuo. Dissolve the residue in ethyl acetate (50 mL) and adjust to pH 8 with saturated NaHCO$_3$. Extract the aqueous layer with ethyl acetate (2×50 mL). Combine the organic layers, dry (Na$_2$SO$_4$), filter, and concentrate in vacuo. Purify the residue by silica gel chromatography (80 g, eluting with a gradient of 10% to 20% methanol/ethyl acetate, 1.5 L) to provide 4-(4-(3-(trifluoromethoxy)phenyl)-1H-imidazol-2-yl)piperidine (491 mg, 45%).

MS (APCI): m/z=312 [M+H].

Preparation 41

4-(N-Hydroxycarbamimidoyl)-piperidine-1-carboxylic acid tert-butyl ester

Dissolve hydroxylamine hydrochloride (1.65 g; 4.99 equiv; 23.74 mmoles) in water (5 mL) and add sodium carbonate (2.53 g; 23.87 mmoles). Place 4-cyano-piperidine-1-carboxylic acid tert-butyl ester (1 g; 1.00 equiv; 4.76 mmoles) (Astatech) in a small vial and dissolve in methanol (6 mL; 148.25 mmoles), then add to the flask containing the hydroxylamine. Heat the mixture to reflux with stirring and hold for 3 h. Remove the methanol by evaporation and extract the aqueous layer with ethyl acetate (2×100 mL). Wash the combined organics with water (1×100 mL), dry over magnesium sulfate, filter and concentrate to a white solid. Dry under reduced pressure to obtain 1.05 g (91%) of the title compound as a white solid.

LCMS: m/z=188.2 [M−tBu, M+H]

Preparation 42

4-Carbamimidoyl-piperidine-1-carboxylic acid tert-butyl ester

Dissolve 4-(N-Hydroxycarbamimidoyl)-piperidine-1-carboxylic acid tert-butyl ester (9.7 g 1.00 equiv; 39.9 mmoles) in methanol (300 mL) and add acetic acid (2 equiv, 79.73 mmoles; 4.6 mL), and methanol washed Raney Nickel (2.7 g). Heat the reaction to 50° C., then hydrogenate with 1 ATM hydrogen gas for 4.5 hours. Filter the reaction mixture through Celite and concentrate under reduced pressure. Suspend the solid in diethyl ether, filter and dry under reduced pressure to give 10.39 g of 4-carbamimidoyl-piperidine-1-carboxylic acid tert-butyl ester.

MS (ES): m/z=228 [M+H].

Preparation 43

4-Carbamimidoyl-piperidine-1-carboxylic acid tert-butyl ester acetic acid salt

Add 10% Pd/C (0.079 g; 37.12 µmoles) to 4-(N-Hydroxycarbamimidoyl)-piperidine-1-carboxylic acid tert-butyl ester (805 mg; 1.00 equiv; 3.31 mmoles) in acetic acid (15 mL; 261.77 mmoles) and acetic acid anhydride (0.5 mL; 5.29 mmoles). Hydrogenate at room temperature for 7 hr at 20 PSI. Purge flask with nitrogen to provide 1.2 g of a foam. Triturate with acetonitrile and filter to provide 270 mg (28%) of the product as a white solid.

MS (ES): m/z=228.0 [M+H].

Preparation 44

4-[4-(3-Chlorophenyl)-1H-imidazol-2-yl]-piperidine-1-carboxylic acid tert-butyl ester Suspend 4-Diaminomethyl-piperidine-1-carboxylic acid tert-butyl ester acetic acid salt (685 mg; 1.00 equiv; 2.38 mmoles) in dimethylformamide (10 mL; 129.33 mmoles) and add powdered potassium carbonate (1400 mg; 10.13 mmoles). Stir 10 minutes at room temperature then add 2-Bromo-1-(3-chloro-phenyl)-ethanone (1400 mg; 6.00 mmoles) dissolved in 4 mL DMF dropwise to the amidine at room temperature. After 3 h, dilute the reaction with ethyl acetate and wash with 50% aq. sodium bicarbonate. Dry the organic layer over sodium sulfate, filter and concentrate to a crude oil. Purify using ISCO chromatography over a biotage 40M column, eluting with a gradient of DCM to 6% MeOH/DCM. Concentrate the appropriate fractions to give a 20% yield of 4-[4-(3-Chloro-phenyl)-1H-imidazol-2-yl]-piperidine-1-carboxylic acid tert-butyl ester. MS (ES): m/z=262.0 [M+H].

Dissolve 4-[4-(3-Chloro-phenyl)-1H-imidazol-2-yl]-piperidine-1-carboxylic acid tert-butyl ester (171 mg; 472.54 μmoles) in dichloromethane (3 mL; 46.80 mmoles) and slowly add hydrogen chloride (4 mL; 16.00 mmoles) (4M HCl in dioxane) at room temperature. Stir the solution 1 h. Concentrate in vacuo (2×DCM) to give 4-[4-(3-Chloro-phenyl)-1H-imidazol-2-yl]-piperidine hydrochloride salt.

MS (ES): m/z=262.0 [M+H].

The compounds of Preparations 45-47 may be prepared essentially as described in Preparation 44.

| Preparation | Compound | MS (ES): m/z = [M + H] |
|---|---|---|
| 45 | 4-[4-(2,4-Difluoro-phenyl)-1H-imidazol-2-yl]-piperidine hydrochloride salt | 264.0 |
| 46 | 4-[4-(3-Chloro-5-fluoro-phenyl)-1H-imidazol-2-yl]-piperidine hydrochloride | 280.0 |
| 47 | 4-[4-(3-Nitro-phenyl)-1H-imidazol-2-yl]-piperidine hydrochloride | 273.2 |
| 47-A | tert-Butyl 4-(4-(3-bromophenyl)-1H-imidazol-2-yl)piperidine-1-carboxylate | 408.0 |

Preparation 48

Add 4-Cyanopiperidine (7.19 g; 1.00 equiv; 65.269 mmoles); benzaldehyde (1.05 equiv; 68.533 mmoles; 7.0 mL), then sodium triacetoxyborohydride (1.3 eq, 84.85 mmoles; 18.73 g) to 2% (v/v) acetic acid in tetrahydrofuran (435 mL) and stir rapidly until complete. Dilute with ethyl acetate and wash with sat. sodium bicarbonate, saturated aqueous sodium chloride, dry with MgSO₄, filter, evaporate under reduced pressure to give 13.0 g oil. Dissolve in ether (~300 mL), filter, and slowly add 60 mL 1M HCl in ether. Cool in ice bath. Filter, rinse with ether, dry under vacuum and collect 13.616 g (57.51 mmol, 88%) 1-benzyl-piperidine-4-carbonitrile.

MS (ES): m/z=201 [M+H].

Preparation 49

1-Benzyl-piperidine-4-carboximidic acid methyl ester hydrochloride

Dissolve 1-Benzyl-piperidine-4-carbonitrile hydrochloride (1.00 equiv; 57.3 mmoles; 13.57 g) in 75 mL MeOH and cool in ice bath. Saturate with HCl gas for 25 minutes, then remove ice bath and stir for 3 hours. Evaporate under reduced pressure to give 17.47 g (65.0 mmol, 113%) 1-benzyl-piperidine-4-carboximidic acid methyl ester hydrochloride.

MS (ES): m/z=233 [M+H].

Preparation 50

1-Benzyl-piperidine-4-carboxamidine dihydrochloride

Dissolve 1-benzyl-piperidine-4-carboximidic acid methyl ester hydrochloride (17.47 g 1.00 equiv; 65 mmoles) in 2M ammonia in methanol (~350 mL). Saturate with ammonia gas for 15 min. Stir for 18 hours and evaporate. Co-evaporate with dry methanol. Dry under high vacuum to give 18.29 g (63.03 mmol, 97%) of 1-benzyl-piperidine-4-carboxamidine dihydrochloride as a light yellow solid.

MS (ES): m/z=218 [M+H].

Preparation 51

1-Benzyl-4-[5-(3-chloro-4-fluoro-phenyl)-1H-imidazol-2-yl]-piperidine

Dissolve 1-benzyl-piperidine-4-carboxamidine dihydrochloride (2 g; 1.00 equiv; 6.89 mmoles) in dimethylformamide (90 mL). Add powdered potassium carbonate (4 equiv; 27.56 mmoles; 3.8095 g) and warm to ~45° C. Add 3-chloro-4-fluoro-phenacyl bromide (2.00 equiv; 13.782 mmoles; 3.5366 g) in 8 mL with DMF dropwise over 40 minutes. Dilute with 50 mL ethyl acetate, stir 5 min and filter. Evaporate and partition with ethyl acetate/sat. sodium bicarbonate, wash organic layer with water, then saturated aqueous sodium chloride. Dry with MgSO₄, filter and evaporate to red foam. Purify over flash silica gel with 0-10% MeOH/ACN. Pool fractions to give 1.9772 g (5.346 mmol, 78%) 1-Benzyl-4-[5-(3-chloro-4-fluoro-phenyl)-1H-imidazol-2-yl]-piperidine.

MS (ES): m/z=370 [M+H].

The compounds of Preparations 52-53 may be prepared essentially as described in Preparation 51.

| Preparation | Compound | MS (ES): m/z = [M + H] |
|---|---|---|
| 52 | 1-Benzyl-4-[5-(3,4-difluoro-phenyl)-1H-imidazol-2-yl]-piperidine | 368 |
| 53 | 1-Benzyl-4-[4-(4-fluoro-phenyl)-1H-imidazol-2-yl]-piperidine | 336.0 |

Preparation 54

4-[5-(3-chloro-4-fluoro-phenyl)-1H-imidazol-2-yl]-piperidine dihydrochloride

Dissolve 1-benzyl-4-[5-(3-chloro-4-fluoro-phenyl)-1H-imidazol-2-yl]-piperidine (1.00 equiv; 1.595 mmoles; 590 mg); N,N,N',N'-tetramethyl-1,8-naphthalenediamine (1 equiv; 1.595 mmoles; 341.8 mg) in 1,2-dichloroethane (12 mL) and cool in an ice bath. Add 1-chloroethyl chloroformate (3 equiv; 4.785 mmoles; 517 μL) and warm to reflux for 1 hour. Cool to RT and filter through 1 cm plug silica gel, rinse with DCM. Evaporate to give 760 mg foam. Dissolve in MeOH and heat to reflux for 6 hours. Evaporate to give 556.3 mg (99%) 4-[5-(3-chloro-4-fluoro-phenyl)-1H-imidazol-2-yl]-piperidine dihydrochloride as a yellow foam.

MS (ES): m/z=280 [M+H].

The compounds of Preparations 55-56 may be prepared essentially as described in Preparation 54.

| Preparation | Compound | MS (ES): m/z = [M + H] |
|---|---|---|
| 55 | 4-[5-(4-chloro-3-trifluoromethyl-phenyl)-1H-imidazol-2-yl]-piperidine dihydrochloride | 330 |
| 56 | 4-[5-(3,4-dichloro-phenyl)-1H-imidazol-2-yl]-piperidine dihydrochloride | 297 |

Preparation 57

4-[4-(4-Fluoro-phenyl)-1H-imidazol-2-yl]-piperidine

Hydrogenate 1-Benzyl-4-[4-(4-fluoro-phenyl)-1H-imidazol-2-yl]-piperidine in 20% Pd(OH)$_2$/C (Pearlman's catalyst) (0.15 gm) in 125 mL 2B EtOH, at 30° C. for 23 h at 60 PSI. Filter and concentrate to yield the title compound as an oil.

MS (ES): m/z=246.0 [M+H].

The compounds of Preparations 58-59 may be prepared essentially as described in Preparation 57.

| Preparation | Compound | MS (ES): m/z = [M + H] |
|---|---|---|
| 58 | 4-[4-(4-Methoxy-phenyl)-1H-imidazol-2-yl]-piperidine | 258.0 |
| 59 | 4-[4-(3,4-Difluoro-phenyl)-1H-imidazol-2-yl]-piperidine (NH$_4$CO$_2$) | 264.0 |

Preparation 60 tert-Butyl 4-(4-(3-(trifluoromethyl)phenyl)-1H-imidazol-2-yl)piperidine-1-carboxylate Add 4-(4-(3-(trifluoromethyl)phenyl)-1H-imidazol-2-yl)piperidine (795 mg, 2.69 mmol) to a solution of CH$_2$Cl$_2$ (25 mL) and THF (25 mL) under nitrogen followed by triethylamine (0.985 mL, 5.64 mmol) and di-tert-butyl dicarbonate (650 mg, 2.96 mmol). Stir the mixture at room temperature overnight. Concentrate the mixture in vacuo and purify the residue by silica gel chromatography (120 g RediSep column, elute with a gradient of 0% to 100% ethyl acetate/hexanes, over 35 min, 85 mL/min) to provide tert-butyl 4-(4-(3-(trifluoromethyl)phenyl)-1H-imidazol-2-yl)piperidine-1-carboxylate (550 mg, 51%) as an off-white solid.

MS (APCI): m/z=396 [M+H].

The compound of Preparation 61 may be prepared essentially as described in Preparation 60.

| Preparation | Compound | Physical Data |
|---|---|---|
| 61 | tert-Butyl 4-(4-(4-(trifluoromethyl)-phenyl)-1H-imidazol-2-yl)piperidine-1-carboxylate | MS (APCI): m/z = 396 [M + H]. |

Preparation 62 tert-Butyl 4-(1-methyl-4-(3-(trifluoromethyl)phenyl)-1H-imidazol-2-yl)piperidine-1-carboxylate Add tert-butyl 4-(4-(3-(trifluoromethyl)phenyl)-1H-imidazol-2-yl)piperidine-1-carboxylate (540 mg, 1.36 mmol) to diethyl ether (100 mL) and cool to 0° C. Add sodium hydride (55 mg, 1.5 mmol, 60% in mineral oil) to the mixture followed by methyl iodide (0.142 mL, 2.72 mmol). Stir the mixture for 1 h at 0° C. and warm to room temperature. Add THF (40 mL) and stir the mixture for 12 h. Concentrate the mixture, and purify the residue by silica gel chromatography (120 g RediSep column, elute with a gradient of 0% to 100% ethyl acetate:hexane, over 40 min, 85 mL/min) to provide tert-butyl 4-(1-methyl-4-(3-(trifluoromethyl)phenyl)-1H-imidazol-2-yl)piperidine-1-carboxylate (425 mg, 76%).

MS (APCI): m/z=410 [M+H].

The compound of Preparation 63 may be prepared essentially as described in Preparation 62.

| Preparation | Compound | Physical Data |
|---|---|---|
| 63 | tert-Butyl 4-(1-methyl-4-(4-(trifluoromethyl)phenyl)-1H-imidazol-2-yl)piperidine-1-carboxylate | MS (APCI): m/z = 410 [M + H] |
| 63-A | tert-Butyl 4-(4-(3-bromophenyl)-1-methyl-1H-imidazol-2-yl)-piperidine-1-carboxylate | MS (ES): m/z = 422 (M + H) |

Preparation 64

4-(1-Methyl-4-(3-(trifluoromethyl)phenyl)-1H-imidazol-2-yl)piperidine dihydrochloride Add hydrogen chloride (4 M in 1,4-dioxane, 5 mL, 20 mmol) to a solution of tert-5 butyl 4-(1-methyl-4-(3-(trifluoromethyl)phenyl)-1H-imidazol-2-yl)piperidine-1-carboxylate (400 mg, 1.10 mmol) in CH$_2$Cl$_2$ (10 mL) at 0° C. under nitrogen and stir for 2 h. Concentrate the mixture in vacuo to provide 4-(1-methyl-4-(3-(trifluoromethyl)phenyl)-1H-imidazol-2-yl)piperidine dihydrochloride (435 mg, >99%).

MS (APCI): m/z=310 [M+H].

The compound of Preparation 65 may be prepared essentially as described in Preparation 64.

| Preparation | Compound | Physical Data |
|---|---|---|
| 65 | 4-(1-Methyl-4-(4-(trifluoromethyl)-phenyl)-1H-imidazol-2-yl)piperidine dihydrochloride | MS (APCI): m/z = 310 [M + H] |

Preparation 66

4-[4-(4-Fluoro-3-trifluoromethyl-phenyl)-1H-imidazol-2-yl]-piperidine-1-carboxylic acid tert-butyl ester Add ammonium acetate (3.24 g, 41.63 mmoles) to a solution of tert-butyl 4-(2-oxo-2-(4-(trifluoromethyl)phenyl)ethylcarbamoyl)piperidine-1-carboxylate (600 mg, 1.00 equiv; 1.39 mmoles) in 1-Butanol (7 mL), followed by triethylamine (1 equiv; 193.40 μL). Stir the mixture at 160° C. in a sealed tube for 2 hours. Remove the solvent in vacuo by co-evaporating with toluene and CH$_2$Cl$_2$. Redissolve the crude in EtOAc, wash with water, dry over Na$_2$SO$_4$ and concentrate. Purify the residue via silica gel chromatography, eluting with EtOAc:Hexane (6:4) to offer 280 mg (49% yield) of the title compound.

LCMS: MS(IS): m/z=314.2 [M+H].

The compounds of Preparations 67-73 may be prepared essentially as described in Preparation 66.

| Preparation | Compound | Physical Data |
| --- | --- | --- |
| 67 | 4-[4-(4-Fluoro-3-trifluoromethyl-phenyl)-1H-imidazol-2-yl]-3-methyl-piperidine-1-carboxylic acid tert-butyl ester | MS (IS): m/z = 428.2 [M + H] |
| 68 | 4-[4-(4-Cyano-phenyl)-1H-imidazol-2-yl]-piperidine-1-carboxylic acid tert-butyl ester | MS (ES): m/z = 353.2 [M + H] |
| 69 | 4-[4-(4-Fluoro-3-trifluoromethyl-phenyl)-5-methyl-1H-imidazol-2-yl]-piperidine-1-carboxylic acid tert-butyl ester | MS (ES): m/z = 428.2 [M + H] |
| 70 | 4-[4-(3-Cyano-phenyl)-1H-imidazol-2-yl]-piperidine-1-carboxylic acid tert-butyl ester | MS (ES): m/z = 353.2 [M + H] |
| 71 | 4-[4-(2-Chloro-5-trifluoromethyl-phenyl)-1H-imidazol-2-yl]-piperidine-1-carboxylic acid tert-butyl ester | MS (ES): m/z = 430.2 [M + H] |
| 72 | 4-[4-(3-Fluoro-5-trifluoromethyl-phenyl)-1H-imidazol-2-yl]-piperidine-1-carboxylic acid tert-butyl ester | MS (ES): m/z = 414.2 [M + H] |
| 73 | 4-[4-(2-Fluoro-5-trifluoromethyl-phenyl)-1H-imidazol-2-yl]-piperidine-1-carboxylic acid tert-butyl ester | MS (ES): m/z = 414.2 [M + H] |
| 73-A | Tert-butyl 4-(5-methyl-4-(4-(trifluoromethyl)phenyl)-1H-imidazol-2-yl]-piperidine-1-carboxyliate | MS (IS): m/z = 409.2 [M + H] |
| 73-B | Tert-butyl 4-(5-methyl-4-(3-(trifluoromethyl)phenyl)-1H-imidazol-2-yl]-piperidine-1-carboxyliate | MS (IS): m/z = 409.2 [M + H] |
| 73-C | Tert-butyl 4-(5-methyl-4-(3-chloro-4-fluorophenyl)-1H-imidazol-2-yl]-piperidine-1-carboxyliate | MS (IS): m/z = 393.2 [M + H] |
| 73-D | Tert-butyl 4-(5-methyl-4-(3-fluorophenyl)-1H-imidazol-2-yl]-piperidine-1-carboxyliate | MS (IS): m/z = 359.2 [M + H] |

Preparation 74

4-[4-(4-Fluoro-3-trifluoromethyl-phenyl)-1-methyl-1H-imidazol-2-yl]-piperidine-1-carboxylic acid tert-butyl ester Dissolve 4-[4-(4-Fluoro-3-trifluoromethyl-phenyl)-1H-imidazol-2-yl]-piperidine-1-carboxylic acid tert-butyl ester (860 mg, 2.08 mmoles) in diethyl ether (100 mL) under $N_2$. Cool the solution to 0° C. in an ice bath, and add sodium hydride (1.1 equiv; 2.29 mmoles; 91.52 mg), followed by injecting methyl iodide (2.00 equiv; 4.16 mmoles; 259.12 µL). Stir the mixture for 1 hour at 0° C., and then warm to room temperature. Inject tetrahydrofuran (40 mL) into the above mixture, and then stir at room temperature overnight. Concentrate the mixture under reduced pressure, and then dissolve the residue in EtOAc. Wash with saturated aqueous sodium chloride. Purify the residue via silica gel chromatography, eluting with EtOAc:hexane (7:3) to offer 270 mg (30% yield) of a title compound.

MS (IS): m/z=428.2 [M+H].

Preparation 74-A

Tert-Butyl 4-(1,5-dimethyl-4-(4-(trifluoromethyl)phenyl)-1H-imidazol-2-yl]-piperidine-1-carboxylate Add freshly powdered potassium hydroxide (193.45 mg, 2.93 mmols, 4 equiv) to a solution of tert-butyl 4-(5-dimethyl-4-(4-(trifluoromethyl)phenyl)-1H-imidazol-2-yl]-piperidine-1-carboxylate (300 mg, 0.73 mmoles) in dimethyl sulfoxide (2 mL). Stir the mixture at room temperature for one hour, and add methyl iodide (156 mg, 1.5 equiv) in one portion. After stirring for three hours, dilute with AcOEt, wash with saturated aq. sodium chloride and dry over $Na_2SO_4$. Purify the residue via silica gel chromatography, eluting with EtOAc:hexane (6:4) to offer 210 mg (68% yield) of a title compound. MS (IS): m/z=423.2 [M+H].

The compounds of Preparations 74-B to 74-F may be prepared essentially as described in Preparation 74-A.

| Preparation | Compound | MS (IS): m/z = [M + H] |
| --- | --- | --- |
| 74-B | Tert-butyl 4-(1,5-dimethyl-4-(3-(trifluoromethyl)phenyl)-1H-imidazol-2-yl]-piperidine-1-carboxylate | 423.2 |
| 74-C | Tert-butyl 4-(4-(3-chloro-4-(fluorophenyl)-1,5-dimethyl-1H-imidazol-2-yl]-piperidine-1-carboxylate | 407.2 |
| 74-D | Tert-butyl 4-(4-(3-fluorophenyl)-1,5-dimethyl-1H-imidazol-2-yl]-piperidine-1-carboxylate | 373.2 |
| 74-E | tert-Butyl 4-(4-(3,4-difluorophenyl)-1-isopropyl-1H-imidazol-2-yl)piperidine-1-carboxylate | |
| 74-F | tert-butyl 4-(1-isopropyl-4-(3-(trifluoromethyl)phenyl)-1H-imidazol-2-yl)piperidine-1-carboxylate | |

Preparation 75

4-[4-(4-Fluoro-3-trifluoromethyl-phenyl)-1H-imidazol-2-yl]-piperidine hydrochloride Add hydrogen chloride (2 mL, 12 M aqueous) to a solution of 4-[4-(4-Fluoro-3-trifluoromethyl-phenyl)-1H-imidazol-2-yl]-piperidine-1-carboxylic acid tert-butyl ester (275 mg; 665.19 µmoles) in methanol (10 mL). Stir the mixture at room temperature overnight, and then concentrate and dry to offer 210 mg (90% yield) of the title compound.

MS (IS): m/z=314.2 [M+H].

The compounds of Preparations 76-83F may be prepared essentially as described in Preparation 75.

| Preparation | Compound | MS (IS): m/z = [M + H] |
|---|---|---|
| 76 | 4-[4-(4-Fluoro-3-trifluoromethyl-phenyl)-1H-imidazol-2-yl]-3-methyl-piperidine dihydrochloride | 328.2 |
| 77 | 4-[4-(4-Fluoro-3-trifluoromethyl-phenyl)-1-methyl-1H-imidazol-2-yl]-piperidine hydrochloride | 328.2 |
| 78 | 4-[4-(4-Fluoro-3-trifluoromethyl-phenyl)-5-methyl-1H-imidazol-2-yl]-piperidine dihydrochloride salt | 328.2 |
| 79 | 4-(2-Piperidin-4-yl-1H-imidazol-4-yl)-benzonitrile dihydrochloride salt | 253.2 |
| 80 | 3-(2-Piperidin-4-yl-1H-imidazol-4-yl)-benzonitrile dihydrochloride salt | 253.2 |
| 81 | 4-[4-(2-Chloro-5-trifluoromethyl-phenyl)-1H-imidazol-2-yl]-piperidine dihydrochloride salt | 330.2 |
| 82 | 4-[4-(3-Fluoro-5-trifluoromethyl-phenyl)-1H-imidazol-2-yl]-piperidine dihydrochloride salt | 314.2 |
| 83 | 4-[4-(2-Fluoro-5-trifluoromethyl-phenyl)-1H-imidazol-2-yl]-piperidine dihydrochloride salt | 314.2 |
| 83-A | 4-(1,5-dimethyl-4-(4-(trifluoromethyl)phenyl)-1H-imidazol-2-yl)-piperidine hydrochloride salt | 323.2 |
| 83-B | 4-(1,5-dimethyl-4-(3-(trifluoromethyl)phenyl)-1H-imidazol-2-yl)piperidine hydrochloride salt | 323.2 |
| 83-C | 4-(4-(3-chloro-4-fluorophenyl)-1,5-dimethyl-1H-imidazol-2-yl)piperidine hydrochloride salt | 307.2 |
| 83-D | 4-(4-(3-fluorophenyl)-1,5-dimethyl-1H-imidazol-2-yl)piperidine hydrochloride salt | 273.2 |
| 83-E | 4-[4-(3,4-Difluoro-phenyl)-1-isopropyl-1H-imidazol-2-yl]-piperidine hydrochloride salt | |
| 83-F | 4-(1-Isopropyl-4-(3-(trifluoromethyl)phenyl)-1H-imidazol-2-yl)piperidine hydrochloride salt | |
| 83-G | 4-(4-(3-Bromophenyl)-1-methyl-1H-imidazol-2-yl)piperidine hydrochloride | 322 |

Preparation 84

1-Benzyl-4-[5-(4-fluoro-3-trifluoromethyl-phenyl)-1H-imidazol-2-yl]-Piperazine

Heat 4-Benzylpiperazine-1-carboxamidine hemisulfate (500 mg, 1.00 equiv; 1.580 mmoles); sodium carbonate (4 equiv, 6.321 mmoles); dimethylformamide (10.5 mL), and acetone (110. mL) to reflux. Add 2-Bromo-1-[4-fluoro-3(trifluoromethyl)phenyl]-1-ethanone (1.00 equiv; 1.580 mmoles; 450 mg) in 4 mL acetone dropwise over 15 minutes and stir the reaction for 30 minutes, then cool to room temperature. Filter the reaction and concentrate under reduced pressure, dilute with ethyl acetate, wash with 20% sat. sodium bicarbonate, water, and saturated aqueous sodium chloride. Dry with MgSO$_4$, filter and evaporate under reduced pressure. Purify the on silica gel with 2-5% 1M NH$_3$-MeOH/DCM to give 262.0 mg (0.678 mmol, 43%) 1-Benzyl-4-[5-(4-fluoro-3-trifluoromethyl-phenyl)-1H-imidazol-2-yl]-piperazine.

MS (ES): m/z=405 [M+H].

Preparation 85

1-[5-(4-Fluoro-3-trifluoromethyl-phenyl)-1H-imidazol-2-yl]-piperazine

Combine 1-Benzyl-4-[5-(4-fluoro-3-trifluoromethyl-phenyl)-1H-imidazol-2-yl]-piperazine (260 mg, 1.00 equiv; 0.643 mmoles), 20 wt % Pd(OH)$_2$/C Degussa E101NE/W (250 mg); methanol (10 mL), formic acid, ammonium salt (20 equiv, 12.8 mmoles; 810 mg) and heated to 50° C. for 2 hours, then cooled to room temperature. Filter the reaction mixture through Celite®, evaporate under reduced pressure and coevaporate once with methanol to give 195.2 mg (0.621 mmol, 97%) 1-[5-(4-Fluoro-3-trifluoromethyl-phenyl)-1H-imidazol-2-yl]-piperazine as a yellow foam.

MS (ES): m/z=315 [M+H].

Preparation 86

1-Benzyl-4-[4-(3-chloro-4-fluoro-phenyl)-1-ethyl-1H-imidazol-2-yl]-piperidine

Add dimethyl sulfoxide (0.3 M, 2.7 mL) to powdered potassium hydroxide (1.5 equiv, 1.217 mmoles; 68 mg). Add 1-Benzyl-4-[5-(3-chloro-4-fluoro-phenyl)-1H-imidazol-2-yl]-piperidine (300 mg, 1.00 equiv; 0.811 mmoles), dropwise add iodoethane (1.1 equiv, 0.892 mmoles; 71 µL) over 8 min. Stir the reaction for 60 minutes, then dilute with water (120 mL) plus saturated sodium chloride (25 mL) and extract four times with DCM. Wash the organic extracts with water, then saturated aqueous sodium chloride, and dry with MgSO$_4$. Filter and purify on silica gel with 10% methanol/acetonitrile to give 262 mg (0.659 mmol, 81%) of 1-Benzyl-4-[4-(3-chloro-4-fluoro-phenyl)-1-ethyl-1H-imidazol-2-yl]-piperidine.

MS (ES): m/z=398 [M+H].

The compounds of Preparations 87-89 may be prepared essentially as described in Preparation 86.

| Preparation | Compound | MS (ES): m/z = [M + H] |
|---|---|---|
| 87 | 1-Benzyl-4-[4-(3-chloro-4-fluoro-phenyl)-1-methyl-1H-imidazol-2-yl]-piperidine | 384 |
| 88 | 1-Benzyl-4-[4-(3-chloro-4-fluoro-phenyl)-1-isopropyl-1H-imidazol-2-yl]-piperidine | 412 |
| 89 | 1-Benzyl-4-[4-(3,4-difluoro-phenyl)-1-methyl-1H-imidazol-2-yl]-piperidine | 412 |

Preparation 90

4-[4-(3-Chloro-4-fluoro-phenyl)-1-ethyl-1H-imidazol-2-yl]-piperidine hydrochloride Dissolve 1-Benzyl-4-[4-(3-chloro-4-fluoro-phenyl)-1-ethyl-1H-imidazol-2-yl]-piperidine (263.3 mg, 1.00 equiv; 0.662 mmoles) and 1,8-Naphthalenediamine, N,N,N',N'-Tetramethyl-(0.05 equiv, 0.033 mmoles, 7.0 mg) in 1,2-Dichloro-ethane (5 mL) and cool in an ice bath. Add 1-chloroethyl chloroformate (1.2 equiv, 0.794 mmol; 0.086 mL). Stir the reaction 10 minutes in an ice bath then heat to reflux for 20 minutes and evaporate to dryness. Dissolve the residue in methanol (5 mL) and reflux for 45 minutes and evaporate to dryness to give 268 mg (0.779 mmol, 118%) 4-[4-(3-chloro-4-fluoro-phenyl)-1-ethyl-1H-imidazol-2-yl]-piperidine hydrochloride.

MS (ES): m/z=308 [M+H].

The compounds of Preparations 91-93 may be prepared essentially as described in Preparation 90.

| Preparation | Compound | MS (ES):<br>m/z = [M + H] |
|---|---|---|
| 91 | 4-[4-(3-Chloro-4-fluoro-phenyl)-1-methyl-1H-imidazol-2-yl]-piperidine hydrochloride | 294 |
| 92 | 4-[4-(3-Chloro-4-fluoro-phenyl)-1-isopropyl-1H-imidazol-2-yl]-piperidine hydrochloride | 440.2 |
| 93 | 4-[4-(3,4-Difluoro-phenyl)-1-methyl-1H-imidazol-2-yl]-piperidine | 278.0 |

Preparation 94

4-Chloro-5-fluoro-7H-pyrrolo[2,3-d]pyrimidine

Combine 4-Chloropyrrolo[2,3-d]pyrimidine (2.985 g, 19.40 mmol), [1-(chloromethyl)-4-fluoro-1,4-diazoniabicyclo[2.2.2]octanebis(tetrafluoroborate)] (Selectfluor) (10.523 g, 29.704 mmol)], acetonitrile (200 mL), and acetic acid (40 mL) and heat to 70° C. for 24 hours. Monitor loss of starting material by HPLC then concentrate. Add two portions of toluene (50 mL) and evaporate. Filter crude material thru a pad of celite, washing with 1:1 EtOAc/CH$_2$Cl$_2$. Finally, concentrate the filtrate and chromatograph on a silica column eluting with CH$_2$Cl$_2$/MeOH [0-10% MeOH gradient]. Check fractions by MS and combine product fractions to provide 1.931 g (58%) of 4-Chloro-5-fluoro-7H-pyrrolo[2,3-d]pyrimidine.

MS (ES): m/z=172 [M+H]

Preparation 95

4-Chloro-1H-pyrazolo[3,4-d]pyrimidine

To a solution of allopurinol (20 g, 146.94 mmoles) in toluene (205.71 mL), add phosphoryl chloride (68.27 mL, 734.68 mmoles) and diisopropylethylamine (56.38 mL, 323.26 mmoles) and heat the mixture at 80° C. for 2 hours. Remove the solvent in vacuo to half and pour the mixture into 2 M potassium phosphate, dibasic (734.68 mL, 1.47 moles) in water at 4° C. Stir the mixture overnight at room temperature. Filter off the precipitate through a pad of celite and wash it subsequently with EtOAc. Separate the filtrate, wash the aqueous layer with more EtOAc, join the organic layers, dry it over MgSO$_4$, filter and concentrate in vacuo to afford 4-Chloro-1H-pyrazolo[3,4-d]pyrimidine (16 g, 70.45% yield) as a yellow solid.

MS (APCI): m/z=155.1 [M+H]

Preparation 95-A

4,6-Dichloropyrimidine-5-carbaldehyde

Charge DMF (8.9 mL, 1.3 eq) in a round bottom flask and cool to 0° C. Add POCl$_3$ (32.6 mL, 4.0 eq) to the reaction drop wise at 0° C. Stir the reaction mass at 0° C. for 1 h. Charge 4,6-dihydroxy pyrimidine (10.0 g, 1.0 eq) to the reaction mass and allowed it to come to room temperature slowly. Reflux the reaction mass for 4 h and monitor the reaction by TLC (10% acetone in DCM). Concentrate the reaction mass under vacuum and pour the concentrated reaction mass over crushed ice. Extract the product with diethyl ether and wash with saturated aq. sodium chloride. Dry the organic layer over anhydrous sodium sulfate and concentrate it under vacuum to get pale yellow solid as product (6.2 g, 40%).

Preparation 95-B

1-(4,6-Dichloropyrimidin-5-yl)propan-1-ol

Charge 4,6-dichloro-pyrimidine-5-carbaldehyde (2.5 g, 1.0 eq) and toluene (50 mL) in a round bottom flask. Cool the reaction mass to −10° C. Add ethyl magnesium bromide (3M) in THF solution (5.1 mL, 1.1 eq) drop wise at −10° C. Slowly allow the reaction mass to come to RT in 1 h. Charge chilled ammonium chloride solution to the reaction mass and extract with diethyl ether. Wash ether layer with saturated aq. sodium chloride solution. Dry the ether layer over anhydrous sodium sulfate and concentrated it under reduced pressure to get the desired product (2.3 g, 79.3%).

The compound of Preparation 95-C may be prepared essentially as described in Preparation 95-B.

| Preparation | Compound |
|---|---|
| 95-C | 1-(4,6-Dichloropyrimidin-5-yl)ethanol |

Preparation 95-D

4-Chloro-3-iodo-1H-pyrazolo[3,4-d]pyrimidine

Charge 4-chloro-1H-pyrazolo[3,4-d]pyrimidine (6.1 g, 1.0 eq), N-iodosuccinimide (NIS) (21.55 g, 2.0 eq) and DMF (213.5 mL) in a round bottom flask. Stir the reaction mass at 50° C. for 16 h. Monitor the reaction by TLC (10% acetone in DCM). Concentrate the reaction mass under reduced pressure. Charge ethyl acetate and wash with water and saturated aq. sodium chloride. Dry the organic layer over anhydrous sodium sulfate and concentrate the organic layer under reduced pressure to give 4-chloro-3-iodo-1H-pyrazolo[3,4-d]pyrimidine (6.8 g, 61.43%).

Preparation 95-E

4-Chloro-3-((trimethylsilyl)ethynyl)-1H-pyrazolo[3,4-d]pyrimidine

Charge 4-chloro-3-iodo-1H-pyrazolo[3,4-d]pyrimidine (5.4 g, 1.0 eq), trimethyl silyl acetylene (11.347 g, 6.0 eq), CuI (1.833 g, 0.5 eq), TEA (2.68 mL, 1.0 eq), DMF (67.5 mL), and THF (202.5 mL) in a round bottom flask under argon atmosphere. Stir the reaction mass under argon atm for 30 min. Charge (PPh$_3$)$_4$Pd (2.225 g, 0.1 eq) and stir the reaction mass at 35° C. for 3 h. Monitor the reaction by TLC (10% acetone in DCM). Concentrate the reaction mass under reduced pressure. Charge ethyl acetate and wash with saturated sodium bicarbonate solution, water and saturated aq. sodium chloride. Dry the organic layer over anhydrous sodium sulfate and concentrate the organic layer under reduced pressure. Purify the compound by column chromatography (silica 100-200 mesh, DCM-Acetone) to give desired product (1.81 g, 36.14%).

Preparation 96

Cyclopropyl-(4,6-dichloro-pyrimidin-5-yl)-methanol

Add slowly n-BuLi (2.37 g, 36.0 mmol) to a cooled solution of diisopropylamine (3.72 g, 36.0 mmol) in 50.0 mL THF at −78° C. under nitrogen atmosphere. Stir the reaction mixture for 30 min at the same temperature, then add 4,6-dichloropyrimidine (5.0 g, 33.0 mmol) dissolved in 15 mL of THF. Stir the resultant reaction mixture for an additional 30 min at −78° C., then add cyclopropane carbaldehyde (2.58 g, 36.8 mmol). Allow the reaction mixture to warm up to room temperature. Add 50.0 mL of water and extract the organic with ethyl acetate (3×50 mL), wash with saturated aqueous sodium chloride, then dry over anhydrous sodium sulfate. Concentrate under reduced pressure under vacuum to give Cyclopropyl-(4,6-dichloro-pyrimidin-5-yl)-methanol (4.0 g, 54% yield). MS (APCI): m/z=220 [M+H]

Preparation 97

Cyclopropyl-(4,6-dichloro-pyrimidin-5-yl)-methanone

Add chromium oxide (VI) (5.84 g, 58.4 mmoles) portion wise to cyclopropyl-(4,6-dichloro-pyrimidin-5-yl)-methanol (4.0 g, 18.2 mmoles) in 80.0 mL acetone at 0° C. and stirr for 30 min at 0° C. Next add isopropyl alcohol to quench the excess reagent and stir for another 15 min at room temperature. Cool to 0° C. and pour onto sat. NaHCO$_3$ solution. Filter through Celite® bed, extract with ethyl acetate (3×50 mL), and wash the combined organic layers with saturated aqueous sodium chloride. Dry and concentrate under reduced to give the title compound as a colorless oil (2.0 g, Yield 50%, 9.2 mmol).

MS (ES): m/z=218 [M+H].

The following Preparations may be prepared essentially as described in Preparation 97.

| Preparation | Compound |
| --- | --- |
| 97-A | 1-(4,6-dichloropyrimidin-5-yl)propan-1-one |
| 97-B | 1-(4,6-dichloropyrimidin-5-yl)ethanone |

Preparation 98

4-Chloro-3-cyclopropyl-1H-pyrazolo[3,4-d]pyrimidine

Add hydrazine hydrate (2.67 g, 53.4 mmol) slowly to cyclopropyl-(4,6-dichloro pyrimidin-5-yl)-methanone (9.66 g, 44.5 mmol) dissolved in 300 mL THF at room temperature and stir for 4 hours. Upon completion, partition the reaction mixture between water and ethyl acetate, collect the organic layer, wash with saturated aqueous sodium chloride, dry over anhydrous sodium sulfate, and concentrate under vacuum. Purify the resultant title compound by passing through a short silica gel (60-120 mesh) pad using Chloroform/methanol (97:3) as eluent.

MS (ES): m/z=195 [M+H].

Preparation 99

4-(3-Trifluoromethyl-phenyl)-1H-imidazole

Add formamide (15 mL; 32.72 equiv; 376.99 mmoles; 15.00 mL; 16.98 g) and 2-Bromo-1-(3-trifluoromethyl-phenyl)-ethanone (3.077 g; 1.00 equiv; 11.52 mmoles; 3.08 g) to a sealed tube and heat to 185° C. for 3 hours. Pour the reaction into NaHCO$_3$ and dilute with EtOAc, wash with water, saturated aqueous sodium chloride and dry over Na$_2$SO$_4$, filter, and concentrate to dryness. Take the crude mixture and purify by flash chromatography on silica eluting with dichloromethane (DCM)/methanol 0-10%. Collect fractions with product and remove solvent to give 4-(3-Trifluoromethyl-phenyl)-1H-imidazole (1.373 g; 0.56 equiv; 6.47 mmoles; 1.37 g; 56.16% yield).

MS (ES): m/z=213.0 [M+H].

The compound of Preparation 100 may be prepared essentially as described in Preparation 99.

| Preparation | Compound | Physical Data |
| --- | --- | --- |
| 100 | 4-(4-Trifluoromethyl-phenyl)-1H-imidazole | MS (ES): m/z = 213.0 [M + H] |

Preparation 101

4-(3-Trifluoromethyl-phenyl)-1-(2-trimethylsilanyl-ethoxymethyl)-1H-imidazole

To a 250 mL round bottom flask (fitted with rubber septum and nitrogen blanket and stir bar) add Tetrahydrofuran (30 mL; 368.66 mmoles; 30.00 mL; 26.58 g), 4-(3-Trifluoromethyl-phenyl)-1H-imidazole (1.047 g; 1.00 equiv; 4.93 mmoles; 1.05 g) and cool the mixture to 0° C. with stirring on and hold for 5 min. Add sodium hydride (0.138 g; 1.11 equiv; 5.46 mmoles; 138.00 mg) to the flask and stir the reaction for 20 min. Add 2-(trimethylsilyl)ethoxymethyl chloride (1.15 mL; 1.31 equiv; 6.49 mmoles; 1.15 mL; 1.08 g) and allow the reaction to warm to room temperature. Dilute the reaction with water and extract the mixture two times with ethyl acetate and discard the aqueous phase. Dry the material over Na$_2$SO$_4$, filter, and concentrate to dryness. Purify the crude mixture by flash chromatography on silica gel eluting with ethyl acetate/hexane from 10-60% EtOAc. Combine the appropriate fractions and concentrated to give 4-(3-Trifluoromethyl-phenyl)-1-(2-trimethylsilanyl-ethoxymethyl)-1H-imidazole (1.178 g; 0.70 equiv; 3.44 mmoles; 1.18 g; 69.71% yield).

MS(ES): (m/z)=343.2 [M+H].

The compound of Preparation 102 may be prepared essentially as described in Preparation 101.

| Preparation | Compound | Physical Data |
|---|---|---|
| 102 | 4-(4-Trifluoromethyl-phenyl)-1-(2-trimethylsilan-yl-ethoxymethyl)-1H-imidazole | MS (ES): (m/z) = 343.2 [M + H] |

Preparation 103

4-Hydroxy-4-[4-(3-trifluoromethyl-phenyl)-1-(2-trimethylsilanyl-ethoxymethyl)-1H-imidazol-2-yl]-piperidine-1-carboxylic acid tert-butyl ester To a 100 mL round bottom flask (fitted with cooling bath, stir bar and nitrogen blanket) add 4-(3-Trifluoromethyl-phenyl)-1-(2-trimethylsilanyl-ethoxymethyl)-1H-imidazole (0.995 g; 1.00 equiv; 2.91 mmoles; 995.00 mg), n-Butyl Lithium (2.8 mL; 1.54 equiv; 4.48 mmoles; 2.80 mL; 1.90 g), and Tetrahydrofuran (30 mL; 368.66 mmoles; 30.00 mL; 26.58 g) and cool the mixture to −78° C. with stirring on and hold for 30 min. Add N-T-Butoxycarbonyl-4-piperidone (0.706 g; 1.22 equiv; 3.54 mmoles; 706.00 mg) and allow the reaction to warm to room temperature. Dilute the reaction with $CH_2Cl_2$, wash with water, dry over $Na_2SO_4$, filter, and concentrate to dryness. Purify the crude mixture by flash chromatography on silica eluting with ethyl acetate/hexane from 10-50% EtOAc. Combine the appropriate fractions and concentrate to give 4-Hydroxy-4-[4-(3-trifluoromethyl-phenyl)-1-(2-trimethylsilanyl-ethoxymethyl)-1H-imidazol-2-yl]piperidine-1-carboxylic acid tert-butyl ester (1.248 g; 0.79 equiv; 2.30 mmoles; 1.25 g; 79.29% yield).

MS(ES): (m/z)=542.2 [M+H].

The compound of Preparation 104 may be prepared essentially as described in Preparation 103.

| Preparation | Compound | Physical Data |
|---|---|---|
| 104 | 4-Hydroxy-4-[4-(4-trifluoromethyl-phenyl)-1-(2-trimethylsilanyl-ethoxymethyl)-1H-imidazol-2-yl]-piperidine-1-carboxylic acid tert-butyl ester | MS (ES): (m/z) = 542.2 [M + H] |

Preparation 105

4-[4-(3-Trifluoromethyl-phenyl)-1H-imidazol-2-yl]-piperidin-4-ol

To a microwave vial add 4-hydroxy-4-[4-(3-trifluoromethyl-phenyl)-1-(2-trimethylsilanyl-ethoxymethyl)-1H-imidazol-2-yl]-piperidine-1-carboxylic acid tert-butyl ester (0.453 g; 1.00 equiv; 836.28 µmoles; 453.00 mg), ethanol (5 mL; 85.88 mmoles; 5.00 mL; 3.96 g), and hydrogen chloride (5 mL; 5.00 mmoles; 1N aqueous) and heat to 70° C. in a microwave with stirring on and hold for 4 h. Concentrate the reaction mixture to give 4-[4-(3-Trifluoromethyl-phenyl)-1H-imidazol-2-yl]-piperidin-4-ol salt (0.32 g; 1.00 equiv; 832.84 µmoles; 320.00 mg; 99.59% yield).

MS(ES): (m/z)=312.2 [M+H].

The compound of Preparation 106 may be prepared essentially as described in Preparation 105.

| Preparation | Compound | Physical Data |
|---|---|---|
| 106 | 4-[4-(4-Trifluoromethyl-phenyl)-1H-imidazol-2-yl]-piperidin-4-ol | MS (ES): (m/z) = 312.2 [M + H] |

Preparation 107

1-Methyl-4-phenyl-1H-imidazole

Add 20 mL dimethyl sulfoxide (35 mL; 492.74 mmoles) to powdered potassium hydroxide (20.81 mmoles; 1.17 g). Add 5-phenyl-1H-imidazole (13.87 mmoles; 2.00 g) at room temperature and solid quickly dissolves giving an orange solution. After stirring 5 min add methyl iodide (15.26 mmoles; 950.36 µL) in one portion. Stir 4h at room temp. Dilute with water and extract with ethyl acetate (2×), then wash the organics with saturated aq. sodium chloride/water (2×) solution, dry over $MgSO_4$, filter, evaporate to give 1.71 g yellow solid. Purify the crude by using ISCO chromatography over a biotage 40M column eluting with a gradient of 0.5% MeOH/DCM to 5% MeOH/DCM at a flow rate of 40 mL/min. Dry product fractions to give 1.43 g (65% yield) off-white solid. (7% of undesired regioisomer) MS (ES): (m/z)=159.0 [M+H].

Preparation 108

4-(1-Methyl-4-phenyl-1H-imidazol-2-yl)-piperidin-4-ol dihydrochloride

Dissolve 1-methyl-4-phenyl-1H-imidazole (9.05 mmoles; 1.43 g) in anhydrous tetrahydrofuran (30.00 mL) and the mixture cooled to −78° C. Slowly add n-butyl lithium (1.30 equiv; 11.77 mmoles; 7.35 mL) (1.6M in hexanes) and the reaction stirs at −78° C. for 30 minutes then add a THF (20 mL) solution of N-T-butoxycarbonyl-4-piperidone (11.77 mmoles; 2.34 g) dropwise over 20 min. Allow to stir overnight with warming to room temperature. Dilute with DCM and saturated aq. sodium chloride/water (50/50), (2×DCM), then dry over $MgSO_4$. Filter and concentrate to 3.8 g crude yellow oil. Purify the reaction by using ISCO chromatography over a Biotage 40M column eluting with 50:50 EtOAc:Hex at a flow rate of 40 mL/min. Concentrate product fractions to 2.00 g of 4-hydroxy-4-(1-methyl-4-phenyl-1H-imidazol-2-yl)-piperidine-1-carboxylic acid tert-butyl ester as a white solid. ES-MS (M+H)=358.3. Dissolve it in 5 mL dichloromethane and add hydrogen chloride (20.00 mmoles; 5.00 mL)(4M in dioxane) slowly at room temperature. After approximately 5 min the solution becomes cloudy and add 3 mL of methanol to get the reaction back into solution. After 1 h the reaction is 95% complete. Add 1 mL of 4M HCl in dioxane and stir 15 min. Concentrate to 2.1 g of 4-(1-Methyl-4-phenyl-1H-imidazol-2-yl)-piperidin-4-ol dihydrochloride as a light yellow solid. MS(ES): (m/z)=258.3 [M+H].

Preparation 109

4-Chloro-5-iodo-7H-pyrrolo[2,3-d]pyrimidine

Dissolve 6-chloro-7-deazapurine (10.75 g, 70 mmol) and N-iodosuccinimide (16.8 g, 75 mmol) in 400 mL of dry DMF and leave at ambient temperature in the darkness over night. Evaporate the solvent. Distribute the dark residue between 500 mL of ethyl acetate and 150 mL of 10% $Na_2SO_3$. Wash the organic fraction with 10% Na₂SO₃ (2×100 mL), saturate aqueous sodium chloride solution (150 mL), dry over Na₂SO₄ and evaporate. Crystallize the yellow residue from ethanol to yield 16.2 g (83%) of 4-chloro-5-iodo-7H-pyrrolo[2,3-d]pyrimidine as off-white crystals. Evaporate the mother liquor, dissolve in toluene, and purify by flush chromatography on silica gel (7×4 cm). Wash the column with toluene until the eluant is colourless then elute the title compound with 5% ethyl acetate in toluene to give an additional 3.5 g of the product.

Preparation 110

4-(4-Chloro-7H-pyrrolo[2,3-d]pyrimidin-5-yl)-2-methylbut-3-yn-2-ol

Charge 4-chloro-5-iodo-7H-pyrrolo[2,3-]pyrimidine (5.0 g, 1.0 eq), 2-methyl-3-butyn-2-ol (9.02 g, 6.0 eq), TEA (1.68 g, 0.93 eq), CuI (1.36 g, 0.4 eq), DMF (62.5 mL) and THF (187.5 mL) at RT under argon atmosphere. Stir the reaction mass at RT under argon atmosphere for 5 min. Charge Pd(PPh₃)₄ (1.03 g, 0.05 eq) and stir the reaction mass at 45° C. for 16 h. Monitor the reaction by TLC (65% CHCl₃: 23% Hexane: 12% Acetone). Concentrate the reaction mass under vacuum. Charge ethyl acetate and give washing with water and saturated aq. sodium chloride. Dry the organic layer over anhydrous Na₂SO₄ and concentrate it under vacuum. Crystallize the compound in 65% CHCl₃: 23% hexane: 12% Acetone to give the desired compound (3.35 g, 79.7%).

The compound of Preparation 111-112 may be prepared essentially as described in Preparation 110.

| Preparation | Compound | Physical Data |
|---|---|---|
| 111 | 3-(4-Chloro-7H-pyrrolo[2,3-d]pyrimidin-5-yl)prop-2-yn-1-ol | |
| 112 | 4-Chloro-5-trimethylsilanylethynyl-7H-pyrrolo[2,3-d]-pyrimidine | LCMS = 250 (M + H) |

Preparation 113

4-Chloro-5-(3-methyl-3-(trimethylsilyloxy)but-1-ynyl)-7H-pyrrolo[2,3-d]pyrimidine Charge 4-(4-chloro-7H-pyrrolo[2,3-d]pyrimidin-5-yl)-2-methylbut-3-yn-2-ol (3.35 g, 1.0 eq), imidazole (2.9 g, 3.0 eq), TEA (2.16 g, 1.5 eq) and diethyl ether (84 mL) at RT. Cool the reaction mass to 0° C. and add trimethyl silyl chloride (1.53 g, 1.0 eq). Stir the reaction mass at RT for 4 h. Monitor the reaction by TLC (5% MeOH in DCM). Charge chilled DM water and extract with diethyl ether. Wash the ether layer with saturated aq. sodium chloride. Dry the organic layer over anhydrous Na₂SO₄ and concentrate it under vacuum to get the desired compound (3.06 g, 70%).

| Preparation | Compound | Physical Data |
|---|---|---|
| 114 | 4-Chloro-5-(3-(trimethylsilyloxy)prop-1-ynyl)-7H-pyrrolo[2,3-d]pyrimidine | |

EXAMPLE 1

4-(4-(5-(2,4-Dichlorophenyl)-1H-imidazol-2-yl)piperidin-1-yl)-1H-pyrazolo[3,4-d]-pyrimidine hydrochloride Heat a mixture of 4-(4-(2,4-dichlorophenyl)-1H-imidazol-2-yl)piperidine (270 mg, 0.91 mmol), 4-chloro-1H-pyrazolo[3,4-d]pyrimidine (280 mg, 1.82 mmol), Et₃N (0.63 mL, 4.5 mmol), and 2-propanol (10 mL) at 90° C. overnight under N₂. Cool the mixture to room temperature and pour into water (100 mL). Extract the mixture with CH₂Cl₂ (2×200 mL), combine the organic layers, and wash with water (50 mL). Dry (Na₂SO₄) the organic layer, filter the mixture, and concentrate the filtrate in vacuo. Purify the residue by silica gel chromatography (25 g of SiO₂, elute with CH₂Cl₂/CMA 4:1, 1000 mL) to provide 4-(4-(5-(2,4-dichlorophenyl)-1H-imidazol-2-yl)piperidin-1-yl)-1H-pyrazolo[3,4-d]pyrimidine (304 mg, 80%). Add hydrochloric acid (2.0 M aqueous, 0.36 mL, 0.72 mmol) to a suspension of 4-(4-(5-(2,4-dichlorophenyl)-1H-imidazol-2-yl)piperidin-1-yl)-1H-pyrazolo[3,4-d]pyrimidine (300 mg, 0.72 mmol) in methanol (7 mL). Concentrate the mixture in vacuo to dryness. Dissolve the residue in methanol (2 mL) and add diethyl ether (50 mL) to form a precipitate. Filter the precipitate, and wash the filter cake with Et₂O. Dissolve the solid in methanol (10 mL) and remove the solvent in vacuo to dryness to provide 4-(4-(5-(2,4-dichlorophenyl)-1H-imidazol-2-yl)piperidin-1-yl)-1H-pyrazolo[3,4-d]pyrimidine hydrochloride (210 mg, 65%) as an off-white solid.

MS (APCI): m/z=414 [M+H].

The compounds of EXAMPLES 2-33 may be prepared essentially as described in EXAMPLE 1.

| EXAMPLE | Compound | Physical Data |
|---|---|---|
| 2 | 4-(4-(4-(4-(Trifluoromethyl)phenyl)-1H-imidazol-2-yl)piperidin-1-yl)-1H-pyrazolo[3,4-d]pyrimidine hydrochloride | MS (APCI): m/z = 414 [M + H] |
| 3 | 4-(4-(4-Phenyl-1H-imidazol-2-yl)piperidin-1-yl)-1H-pyrazolo[3,4-d]pyrimidine hydrochloride | MS (APCI): m/z = 346 [M + H] |
| 4 | 4-(4-(4-(4-Chlorophenyl)-1H-imidazol-2-yl)piperidin-1-yl)-1H-pyrazolo[3,4-d]pyrimidine hydrochloride | MS (APCI): m/z = 380 [M + H] |
| 5 | 4-{4-[4-(3-(Trifluoromethyl)-phenyl)-1H-imidazol-2-yl]-piperidin-1-yl}-1H-pyrazolo[3,4-d]pyrimidine hydrochloride | MS (APCI): m/z = 414 [M + H] |
| 6 | 4-(4-(4-(4-fluoro-3-trifluoromethyl)phenyl)-1H-imidazol-2-yl)piperidin-1-yl)-1H-pyrazolo[3,4-d]pyrimidine hydrochloride | MS (APCI): m/z = 432 [M + H] |

-continued

| EXAMPLE | Compound | Physical Data |
|---|---|---|
| 7 | 4-{4-[4-(4-Fluoro-3-trifluoromethyl-phenyl)-1H-imidazol-2-yl]-piperidin-1-yl}-7H-pyrrolo[2,3-d]pyrimidine hydrochloride | MS (IS): (m/z) = 431.41 [M + H] |
| 8 | 6-{4-[5-(4-Fluoro-3-trifluoromethyl-phenyl)-1H-imidazol-2-yl]-piperidin-1-yl}-9H-purine hydrochloride | MS (IS): (m/z) = 431.41 [M + H] |
| 9 | 5-Fluoro-4-{4-[4-(4-fluoro-3-trifluoromethyl-phenyl)-1H-imidazol-2-yl]-piperidin-1-yl}-7H-pyrrolo[2,3-d]pyrimidine hydrochloride | MS (IS): (m/z) = 449.40 [M + H] |
| 10 | 4-{4-[4-(4-Fluoro-3-trifluoromethyl-phenyl)-1-methyl-1H-imidazol-2-yl]-piperidin-1-yl}-1H-pyrazolo[3,4-d]pyrimidine hydrochloride | MS (IS): (m/z) = 446.2 [M + H] |
| 11 | 4-(4-(1-Methyl-4-((3-trifluoromethyl)phenyl)-1H-imidazol-2-yl)piperidin-1-yl)-1H-pyrazolo[3,4-d]pyrimidine hydrochloride | MS (APCI): m/z = 428 [M + H] |
| 12 | 4-(4-(1-methyl-4-((4-trifluoromethyl)phenyl)-1H-imidazol-2-yl)piperidin-1-yl)-1H-pyrazolo[3,4-d]pyrimidine hydrochloride | MS (APCI): m/z = 428 [M + H] |
| 13 | 4-(4-(3-Fluoro-4-(trifluoromethyl)phenyl)-1H-imidazol-2-yl)piperidin-1-yl)-1H-pyrazolo[3,4-d]pyrimidine hydrochloride | .MS (APCI): m/z = 432 [M + H] |
| 14 | 4-{4-[4-(4-Fluoro-3-trifluoromethyl-phenyl)-1H-imidazol-2-yl]-3-methyl-piperidin-1-yl}-1H-pyrazolo[3,4-d]pyrimidine hydrochloride | MS (IS): (m/z) = 446.2 [M + H] |
| 15 | 4-{4-[4-(4-Fluoro-3-trifluoromethyl-phenyl)-1H-imidazol-2-yl]-3-methyl-piperidin-1-yl}-7H-pyrrolo[2,3-d]pyrimidine hydrochloride | MS (IS): (m/z) = 445.2 [M + H] |
| 16 | 4-{4-[4-(4-Fluoro-3-trifluoromethyl-phenyl)-5-methyl-1H-imidazol-2-yl]-piperidin-1-yl}-7H-pyrrolo[2,3-d]pyrimidine dihydrochloride | MS (IS): (m/z) = 445.2 [M + H] |
| 17 | 4-{4-[4-(4-Fluoro-3-trifluoromethyl-phenyl)-5-methyl-1H-imidazol-2-yl]-piperidin-1-yl}-1H-pyrazolo[3,4-d]pyrimidine dihydrochloride | MS (IS): (m/z) = 446.2 [M + H] |
| 18 | 6-{4-[4-(4-Fluoro-3-trifluoromethyl-phenyl)-5-methyl-1H-imidazol-2-yl]-piperidin-1-yl}-9H-purine dihydrochloride | MS (IS): (m/z) = 446.2 [M + H] |
| 19 | 4-{2-[1-(3-Cyclopropyl-1H-pyrazolo[3,4-d]pyrimidin-4-yl)-piperidin-4-yl]-3H-imidazol-4-yl}-benzonitrile dihydrochloride | MS (IS): (m/z) = 411.2 [M + H] |
| 20 | 4-{2-[1-(1H-Pyrazolo[3,4-d]pyrimidin-4-yl)-piperidin-4-yl]-3H-imidazol-4-yl}-benzonitrile dihydrochloride | MS (IS): (m/z) = 371.2 [M + H] |
| 21 | 3-{2-[1-(1H-Pyrazolo[3,4-d]pyrimidin-4-yl)-piperidin-4-yl]-3H-imidazol-4-yl}-benzonitrile dihydrochloride | MS (IS): (m/z) = 371.2 [M + H] |
| 22 | 3-{2-[1-(3-Cyclopropyl-1H-pyrazolo[3,4-d]pyrimidin-4-yl)-piperidin-4-yl]-3H-imidazol-4-yl}-benzonitrile dihydrochloride | MS (IS): (m/z) = 411.22 [M + H] |
| 23 | 4-{4-[5-(2-Chloro-5-trifluoromethyl-phenyl)-1H-imidazol-2-yl]-piperidin-1-yl}-1H-pyrazolo[3,4-d]pyrimidine dihydrochloride | MS (IS): (m/z) = 448.2 [M + H] |
| 24 | 4-{4-[5-(3-Fluoro-5-trifluoromethyl-phenyl)-1H-imidazol-2-yl]-piperidin-1-yl}-1H-pyrazolo[3,4-d]pyrimidine dihydrochloride | MS (IS): (m/z) = 432.2 [M + H] |
| 25 | 4-{4-[5-(2-Fluoro-5-trifluoromethyl-phenyl)-1H-imidazol-2-yl]-piperidin-1-yl}-7H-pyrrolo[2,3-d]pyrimidine dihydrochloride | MS (IS): (m/z) = 432.2 [M + H] |
| 26 | 4-{4-[5-(2-Fluoro-5-trifluoromethyl-phenyl)-1H-imidazol-2-yl]-piperidin-1-yl}-1H-pyrazolo[3,4-d]pyrimidine dihydrochloride | MS (IS): (m/z) = 432.2 [M + H] |
| 27 | 6-{4-[5-(2-Fluoro-5-trifluoromethyl-phenyl)-1H-imidazol-2-yl]-piperidin-1-yl}-9H-purine dihydrochloride | MS (IS): (m/z) = 432.2 [M + H] |

| EXAMPLE | Compound | Physical Data |
|---|---|---|
| 28 | 3-Cyclopropyl-4-{4-[5-(4-fluoro-3-trifluoromethylphenyl)-1H-imidazol-2-yl]-piperidin-1-yl}-1H-pyrazolo[3,4-d]pyrimidine dihydrochloride | MS (IS): (m/z) = 472.2 [M + H] |
| 29 | 1-(1H-Pyrazolo[3,4-d]pyrimidin-4-yl)-4-[4-(3-trifluoromethyl-phenyl)-1H-imidazol-2-yl]-piperidin-4-ol dihydrochloride | MS (ES): (m/z) = 430.0 [M + H] |
| 30 | 1-(1H-Pyrazolo[3,4-d]pyrimidin-4-yl)-4-[4-(4-trifluoromethyl-phenyl)-1H-imidazol-2-yl]-piperidin-4-ol dihydrochloride | MS (ES): (m/z) = 430.0 [M + H] |
| 30-A | 1-(7H-Pyrrolo[2,3-d]pyrimidin-4-yl)-4-(4-(3-(trifluoromethyl)phenyl)-1H-imidazol-2-yl)piperidin-4-ol dihydrochloride | ES-MS (M + H) = 429.0 |
| 30-B | 1-(9H-Purin-6-yl)-4-(4-(3-(trifluoromethyl)phenyl)-1H-imidazol-2-yl)piperidin-4-ol dihydrochloride | ES-MS (M + H) = 430.0 |
| 30-C | 1-(7H-Pyrrolo[2,3-d]pyrimidin-4-yl)-4-(4-(4-(trifluoromethyl)phenyl)-1H-imidazol-2-yl)piperidin-4-ol dihydrochloride | ES-MS (M + H) = 429.2 |
| 30-D | 1-(9H-Purin-6-yl)-4-(4-(4-(trifluoromethyl)phenyl)-1H-imidazol-2-yl)piperidin-4-ol dihydrochloride | ES-MS (M + H) = 430.0 |
| 31 | 6-{4-[4-(4-Trifluoromethyl-phenyl)-1H-imidazol-2-yl]-piperidin-1-yl}-9H-purine hydrochloride | MS (ES): (m/z) = 414.0 [M + H] |
| 32 | 6-{4-[4-(3-Trifluoromethyl-phenyl)-1H-imidazol-2-yl]-piperidin-1-yl}-9H-purine hydrochloride | MS (ES): (m/z) = 414.0 [M + H] |
| 33 | 4-{4-[4-(4-Fluoro-3-trifluoromethyl-phenyl)-1-methyl-1H-imidazol-2-yl]-piperidin-1-yl}-7H-pyrrolo[2,3-d]pyrimidine hydrochloride | MS (ES): (m/z) = 445.0 [M + H] |
| 33-A | 4-(4-(1,5-dimethyl-4-(4-trifluoromethyl)phenyl)-1H-imidazol-2-yl)piperidin-1-yl)-1H-pyrazolo[3,4-d]pyrimidine dihydrochloride (Coupling reaction in dimethylformamide with diisopropylethylamine) | MS (APCI): m/z = 441 [M + H] |
| 33-B | 4-(4-(1,5-dimethyl-4-(3-trifluoromethyl)phenyl)-1H-imidazol-2-yl)piperidin-1-yl)-1H-pyrazolo[3,4-d]pyrimidine dihydrochloride (Coupling reaction in dimethylformamide with diisopropylethylamine) | MS (APCI): m/z = 441 [M + H] |
| 33-C | 4-(4-(4-(3-chloro-4-fluorophenyl)-1,5-dimethyl-1H-imidazol-2-yl)piperidin-1-yl)-1H-pyrazolo[3,4-d]pyrimidine dihydrochloride (Coupling reaction in dimethylformamide with diisopropylethylamine) | MS (APCI): m/z = 425 [M + H] |
| 33-D | 4-(4-(4-(3-fluorophenyl)-1,5-dimethyl-1H-imidazol-2-yl)piperidin-1-yl)-1H-pyrazolo[3,4-d]pyrimidine dihydrochloride (Coupling reaction in dimethylformamide with diisopropylethylamine) | MS (APCI): m/z = 391 [M + H] |
| 33-E | 6-{4-[4-(3,4-Difluoro-phenyl)-1-isopropyl-1H-imidazol-2-yl]-piperidin-1-yl}-9H-purine hydrochloride | MS (APCI): m/z = 424 [M + H] |
| 33-F | 4-{4-[4-(3,4-Difluoro-phenyl)-1-isopropyl-1H-imidazol-2-yl]-piperidin-1-yl}-1H-pyrazolo[3,4-d]pyrimidine hydrochloride | MS (APCI): m/z = 424 [M + H] |
| 33-G | 4-{4-[1-Isopropyl-4-(3-trifluoromethyl-phenyl)-1H-imidazol-2-yl]-piperidin-1-yl}-7H-pyrrolo[2,3-d]pyrimidine hydrochloride | MS (APCI): m/z = 455 [M + H] |
| 33-H | 4-{4-[1-Isopropyl-4-(3-trifluoromethyl-phenyl)-1H-imidazol-2-yl]-piperidin-1-yl}-1H-pyrazolo[3,4-d]pyrimidine hydrochloride | MS (APCI): m/z = 456 [M + H] |

EXAMPLE 34

4-{4-[5-(4-Fluoro-3-trifluoromethyl-phenyl)-1H-imidazol-2-yl]-piperazin-1-yl}-1H-pyrazolo[3,4-d]pyrimidine hydrochloride Combine 1-[5-(4-Fluoro-3-trifluoromethyl-phenyl)-1H-imidazol-2-yl]-piperazine (195 mg, 1.00 equiv; 0.620 mmoles); 4-Chloro-1H-pyrazolo[3,4-d]pyrimidine (1.00 equiv; 0.620 mmoles; 96 mg); isopropyl alcohol (3 mL); diisopropylethylamine (1 mL) and heat in a microwave reactor at 80° C. for 60 min. Evaporate the reaction mixture and purify on silica gel with 5% MeOH/DCM. Combine the fractions to give 213.2 mg (0.494 mmol, 80%) of 4-{4-[5-(4-Fluoro-3-trifluoromethyl-phenyl)-1H-imidazol-2-yl]-piperazin-1-yl}-1H-pyrazolo[3,4-d]pyrimidine. Dissolve the free base in DCM/MeOH and add 1.0 eq 1M HCl in ether. Concentrate the mixture to give 237.2 mg 4-{4-[5-(4-Fluoro-3-trifluoromethyl-phenyl)-1H-imidazol-2-yl]-piperazin-1-yl}-1H-pyrazolo[3,4-d]pyrimidine hydrochloride.

MS (ES): m/z=443 [M+H].

The following compounds may be prepared essentially as described in EXAMPLE 34.

| EXAMPLE | Compound | Physical Data MS (ES) |
|---|---|---|
| 35 | 4-{4-[5-(3-Chloro-4-fluoro-phenyl)-1H-imidazol-2-yl]-piperidin-1-yl}-1H-pyrazolo[3,4-d]pyrimidine hydrochloride | m/z = 398 [M$^+$ + H] |
| 36 | 4-{4-[5-(4-Chloro-3-trifluoromethyl-phenyl)-1H-imidazol-2-yl]-piperidin-1-yl}-1H-pyrazolo[3,4-d]pyrimidine hydrochloride | m/z = 348 [M$^+$ + H] |
| 37 | 4-{4-[5-(3,4-dichloro-phenyl)-1H-imidazol-2-yl]-piperidin-1-yl}-1H-pyrazolo[3,4-d]pyrimidine hydrochloride | m/z = 414 [M$^+$ + H] |
| 38 | 4-{4-[4-(4-Fluoro-phenyl)-1H-imidazol-2-yl]-piperidin-1-yl}-1H-pyrazolo[3,4-d]pyrimidine hydrochloride | m/z = 364.2 [M$^+$ + H] |
| 39 | 4-{4-[4-(3-Chloro-4-fluoro-phenyl)-1-ethyl-1H-imidazol-2-yl]-piperidin-1-yl}-1H-pyrazolo[3,4-d]pyrimidine hydrochloride | m/z = 426 [M$^+$ + H] |
| 40 | 4-{4-[4-(3-Chloro-4-fluoro-phenyl)-1-methyl-1H-imidazol-2-yl]-piperidin-1-yl}-1H-pyrazolo[3,4-d]pyrimidine hydrochloride | m/z = 412 [M$^+$ + H] |
| 41 | 6-{4-[4-(3-Chloro-4-fluoro-phenyl)-1-methyl-1H-imidazol-2-yl]-piperidin-1-yl}-9H-purine hydrochloride | m/z = 412 [M$^+$ + H] |
| 41-A | 3-Cyclopropyl-4-(4-(4-(4-fluoro-3-(trifluoromethyl)phenyl)-1-methyl-1H-imidazol-2-yl)piperidin-1-yl)-1H-pyrazolo[3,4-d]pyrimidine | MS (M + H): m/z = 486.5 |
| 41-B | 3-Cyclopropyl-4-(4-(4-(3,4-difluorophenyl)-1-methyl-1H-imidazol-2-yl)piperidin-1-yl)-1H-pyrazolo[3,4-d]pyrimidine | MS (M + H): m/z = 436.4 |
| 42 | 4-{4-[4-(3-Chloro-phenyl)-1H-imidazol-2-yl]-piperidin-1-yl}-1H-pyrazolo[3,4-d]pyrimidine hydrochloride | m/z = 380.2 [M$^+$ + H] |
| 43 | 4-{4-[4-(2,4-Difluoro-phenyl)-1H-imidazol-2-yl]-piperidin-1-yl}-1H-pyrazolo[3,4-d]pyrimidine hydrochloride salt | m/z = 382.0 [M$^+$ + H] |
| 44 | 4-{4-[4-(3-Chloro-5-fluoro-phenyl)-1H-imidazol-2-yl]-piperidin-1-yl}-1H-pyrazolo[3,4-d]pyrimidine hydrochloride | m/z = 398.0 [M$^+$ + H] |
| 44-A | 4-{4-[4-(3,4-Difluoro-phenyl)-1-methyl-1H-imidazol-2-yl]-piperidin-1-yl}-7H-pyrrolo[2,3-d]pyrimidine bis hydrochloride | MS (APCI): m/z = 395 [M + H] |
| 44-B | 6-{4-[4-(3,4-Difluoro-phenyl)-1-methyl-1H-imidazol-2-yl]-piperidin-1-yl}-9H-purine bis hydrochloride | MS (APCI): m/z = 396 [M + H] |
| 44-C | 4-{4-[4-(3-Chloro-4-fluoro-phenyl)-1-methyl-1H-imidazol-2-yl]-piperidin-1-yl}-7H-pyrrolo[2,3-d]pyrimidine bis hydrochloride | MS (APCI): m/z = 411 [M + H] |
| 45 | 4-{4-[4-(3-Chloro-4-fluoro-phenyl)-1-isopropyl-1H-imidazol-2-yl]-piperidin-1-yl}-1H-pyrazolo[3,4-d]pyrimidine hydrochloride | m/z = 440.2 [M$^+$ + H] |
| 46 | 4-{4-[4-(3,4-Difluoro-phenyl)-1-methyl-1H-imidazol-2-yl]-piperidin-1-yl}-1H-pyrazolo[3,4-d]pyrimidine hydrochloride | m/z = 396.0 [M$^+$ + H] |
| 47 | 4-{4-[4-(3,4-Difluoro-phenyl)-1H-imidazol-2-yl]-piperidin-1-yl}-1H-pyrazolo[3,4-d]pyrimidine hydrochloride | m/z = 382.0 [M$^+$ + H] |
| 48 | 4-{4-[4-(3-Trifluoromethyl-phenyl)-1H-imidazol-2-yl]-piperidin-1-yl}-7H-pyrrolo[2,3-d]pyrimidine hydrochloride | m/z = 413 [M$^+$ + H] |
| 49 | 4-{4-[1-Methyl-4-(3-trifluoromethyl-phenyl)-1H-imidazol-2-yl]-piperidin-1-yl}-7H-pyrrolo[2,3-d]pyrimidine hydrochloride | m/z = 427 [M$^+$ + H] |
| 50 | 6-{4-[1-Methyl-4-(3-trifluoromethyl-phenyl)-1H-imidazol-2-yl]-piperidin-1-yl}-9H-purine hydrochloride | m/z = 428 [M$^+$ + H] |

| EXAMPLE | Compound | Physical Data MS (ES) |
|---|---|---|
| 50-A | 4-(1-methyl-4-phenyl-1H-imidazol-2-yl)-1-(1H-pyrazolo[3,4-d]pyrimidin-4-yl)piperidin-4-ol (free base) | ES-MS (M + H) = 376.3 |
| 50-B | 4-(1-methyl-4-(3-(trifluoromethyl)phenyl)-1H-imidazol-2-yl)-1-(1H-pyrazolo[3,4-d]pyrimidin-4-yl)piperidin-4-ol (free base) | ES-MS (M + H) = 444.2 |
| 50-C | 4-(1-methyl-4-phenyl-1H-imidazol-2-yl)-1-(9H-purin-6-yl)piperidin-4-ol (free base) | ES-MS (M + H) = 376.2 |
| 50-D | 4-(1-methyl-4-phenyl-1H-imidazol-2-yl)-1-(7H-pyrrolo[2,3-d]pyrimidin-4-yl)piperidin-4-ol (free base) | ES-MS (M + H) = 375.3 |
| 50-E | 1-(3-cyclopropyl-1H-pyrazolo[3,4-d]pyrimidin-4-yl)-4-(1-methyl-4-phenyl-1H-imidazol-2-yl)piperidin-4-ol hydrochloride | ES-MS (M + H) = 416.3 |
| 50-F | 6-(4-(4-(3-bromophenyl)-1-methyl-1H-imidazol-2-yl)piperidin-1-yl)-9H-purine hydrochloride | ES-MS (M + H) = 438.0 |
| 50-G | 4-(4-(4-(3-bromophenyl)-1-methyl-1H-imidazol-2-yl)piperidin-1-yl)-1H-pyrazolo[3,4-d]pyrimidine hydrochloride | ES-MS (M + H) = 438.0 |
| 50-H | 4-(4-(1-methyl-4-phenyl-1H-imidazol-2-yl)piperidin-1-yl)-1H-pyrazolo[3,4-d]pyrimidine hydrochloride | ES-MS (M + H) = 360.3 |
| 50-I | 6-(4-(1-methyl-4-phenyl-1H-imidazol-2-yl)piperidin-1-yl)-9H-purine hydrochloride | ES-MS (M + H) = 360.3 |

EXAMPLE 51

6-(4-(4-(3-(Trifluoromethoxy)phenyl)-1H-imidazol-2-yl)piperidin-1-yl)-7H-purine

Add 4-(4-(3-(trifluoromethoxy)phenyl)-1H-imidazol-2-yl)piperidine (200 mg, 0.642 mmol), 6-chloropurine (105 mg, 0.679 mmol), and triethylamine (95 µL, 0.681 mmol) to 2-propanol (5 mL). Heat the mixture at 80° C. for 3 h. Cool the mixture to room temperature and concentrate in vacuo. Triturate the solid in $CH_2Cl_2$ (10 mL). Purify the remaining solid by silica gel chromatography (60 g, eluting with 40% methanol/methylene chloride, 0.500 L) to provide 6-(4-(4-(3-(trifluoromethoxy)phenyl)-1H-imidazol-2-yl)piperidin-1-yl)-7H-purine (179 mg, 65%).

MS (APCI): m/z=430 [M+H]

EXAMPLE 52

4-{4-[4-(4-Methoxy-phenyl)-1H-imidazol-2-yl]-piperidin-1-yl}-1H-pyrazolo[3,4-d]-pyrimidine Place 4-chloro-1H-pyrazolo[3,4-d]pyrimidine (135 mg; 1.10 equiv; 873.45 µmoles) and 4-[4-(4-Methoxy-phenyl)-1H-imidazol-2-yl]-piperidine (205 mg, 1.00 equiv; 796.63 µmoles; 205.00 mg) in a microwave vial and dissolve in isopropyl alcohol (3 mL; 39.24 mmoles; 3.00 mL). Add diisopropylethylamine (0.5 mL; 2.87 mmoles; 500.00 µL). Heat the mixture to 70° C. in a microwave with stirring on and hold for 1 hr. Dissolve in 5% MeOH/DCM and wash with saturated aqueous sodium bicarbonate. Dry over sodium sulfate, filter and concentrated. Purify using ISCO chromatography over a biotage 40S column eluting with a gradient of 2.5% MeOH/DCM to 10% MeOH/DCM at a flow rate of 40 mL/min. over 35 min collection. Combine the fractions to give 4-{4-[4-(4-Methoxy-phenyl)-1H-imidazol-2-yl]-piperidin-1-yl}-1H-pyrazolo[3,4-d]pyrimidine.

MS (APCI): m/z=376.2 [M+H]

EXAMPLE 53

4-{4-[4-(3-Nitro-phenyl)-1H-imidazol-2-yl]-piperidin-1-yl}-1H-pyrazolo[3,4-d]-pyrimidine Place 4-Chloro-1H-pyrazolo[3,4-d]pyrimidine (150 mg; 1.16 equiv; 970.50 µmoles; 150.00 mg), and 4-[4-(3-Nitrophenyl)-1H-imidazol-2-yl]-piperidine hydrochloride salt (258 mg 1.00 equiv; 835.58 µmoles; 258.00 mg) in a microwave vial and dissolve in isopropyl alcohol (3 mL; 39.24 mmoles; 3.00 mL) and add diisopropylethylamine (0.5 mL; 2.87 mmoles; 500.00 µL). Heat the mixture to 70° C. in a Emrys Optimizer microwave for 1 hour while stirring. Filter, and concentrate filtrate to an oil. Combine solid and oil and dissolve in 3% MeOH/DCM. Purify using ISCO chromatography over a biotage 40S column eluting with a gradient of 2.5% MeOH/DCM to 10% MeOH/DCM at a flow rate of 40 mL/min. Collect appropriate fractions, concentrate to an oil. Dissolve oil in 10% MeOH/DCM and wash with a mixture of aqueous sodium bicarbonate/saturated aqueous sodium chloride three times. Wash the combined organic layers with saturated aqueous sodium chloride and dry over sodium sulfate. Concentrate and dry under reduced pressure to obtain the title compound.

MS (APCI): m/z=391.0 [M+H].

EXAMPLE 53-A 4-(4-(4-(4-fluoro-3-(trifluoromethyl)phenyl)-1-methyl-1H-imidazol-2-yl)piperidin-1-yl)-3-methyl-1H-pyrazolo[3,4-d]pyrimidine In a microwave vial charge 4-[4-(4-fluoro-3-trifluoromethyl-phenyl)-1-methyl-1H-imidazol-2-yl]-piperidine dihydrochloride salt (0.5 g, 1.0 eq), 1-(4,6-dichloro-pyrimidin-5-yl)-ethanone (0.22 g, 1.0 eq), TEA (1.2 mL, 8.0 eq) and isopropyl alcohol (5 mL). Stirr the reaction mass at 80° C. for 45 min in microwave. Monitor the reaction by TLC (10% MeOH in DCM). Cool the reaction mass to 0° C. and add hydrazine hydrate (0.07 mL, 1.2 eq). Slowly bring the reaction mass to RT. Stirr the reaction mass at 80° C. for 45 min in microwave. Monitor the reaction by TLC (10% MeOH in DCM). Concentrate the reaction mass under vacuum. Charge ethyl acetate and then wash with water and saturated aq. sodium chloride. Dry the organic layer over anhydrous Na$_2$SO$_4$ and concentrate it under reduced pressure. Purify the compound by column chromatography (Silica gel 60-120 mesh, DCM-Methanol). Crystallize the product in diethyl ether and filter it to give 4-(4-(4-(4-fluoro-3-(trifluoromethyl)phenyl)-1-methyl-1H-imidazol-2-yl)piperidin-1-yl)-3-methyl-1H-pyrazolo[3,4-d]pyrimidine (0.254 g, 50.29%). MS (M+H): m/z=460.5

The following example may be prepared essentially as described in Example 53-A.

| Example | Compound | Physical Data |
| --- | --- | --- |
| 53-B | 3-Ethyl-4-(4-(4-(4-fluoro-3-(trifluoromethyl)phenyl)-1-methyl-1H-imidazol-2-yl)piperidin-1-yl)-1H-pyrazolo[3,4-d]pyrimidine | MS (M + H): m/z = 474.6 |

EXAMPLE 53-C 3-ethynyl-4-(4-(4-(4-fluoro-3-(trifluoromethyl)phenyl)-1-methyl-1H-imidazol-2-yl)piperidin-1-yl)-1H-pyrazolo[3,4-d]pyrimidine In a microwave vial charge 4-[4-(4-fluoro-3-trifluoromethyl-phenyl)-1-methyl-1H-imidazol-2-yl]-piperidine.2HCl (0.2 g, 1.0 eq), 4-chloro-3-trimethylsilanylethynyl-1H-pyrazolo[3,4-d]pyrimidine (0.151 g, 1.1 eq), diisopropylethylamine (0.72 mL, 7.6 eq) and isopropyl alcohol (6 mL). Stir the reaction mass at 80° C. for 45 min in microwave. Monitor the reaction by TLC (30% Acetone in DCM). Concentrate the reaction mass. Charge ethyl acetate and then wash with water and saturated aq. sodium chloride. Dry the organic layer over anhydrous Na$_2$SO$_4$ and concentrate it under reduced pressure. Purify the compound by column chromatography (Silica gel 100-200 mesh, DCM-Acetone) to give 4-{4-[4-(4-fluoro-3-trifluoromethyl-phenyl)-1-methyl-1H-imidazol-2-yl]-piperidin-1-yl}-3-trimethyl silanylethynyl-1H-pyrazolo[3,4-d]pyrimidine (0.18 g, 60.56%)

Charge 4-{4-[4-(4-fluoro-3-trifluoromethyl-phenyl)-1-methyl-1H-imidazol-2-yl]-piperidin-1-yl}-3-trimethyl silanylethynyl-1H-pyrazolo[3,4-d]pyrimidine (0.18 g, 1.0 eq), KOH (0.057 g, 3.0 eq), MeOH (3.7 mL) and DCM (1.85 mL) in a round bottom flask. Stir the reaction mass at RT for 40 min. Monitor the reaction by TLC (30% Acetone in DCM). Concentrate the reaction mass under vacuum. Charge DCM and given water and saturated aq. sodium chloride washings. Dry the organic layer over anhy. Na$_2$SO$_4$ and concentrated it under vacuum to give 3-ethynyl-4-(4-(4-(4-fluoro-3-(trifluoromethyl)phenyl)-1-methyl-1H-imidazol-2-yl)piperidin-1-yl)-1H-pyrazolo[3,4-d]pyrimidine (0.074 g, 46.07%). LCMS=470.4 (M+1).

The following compound may be prepared essentially as described in Example 53-C.

| Example | Compound | Physical Data |
| --- | --- | --- |
| 53-D | 4-(4-(4-(3,4-Difluorophenyl)-1-methyl-1H-imidazol-2-yl)piperidin-1-yl)-3-ethynyl-1H-pyrazolo[3,4-d]pyrimidine | MS (M + H): m/z = 420.5 |

EXAMPLE 53-E 4-(4-(4-(4-(4-fluoro-3-(trifluoromethyl)phenyl)-1-methyl-1H-imidazol-2-yl)piperidin-1-yl)-7H-pyrrolo[2,3-d]pyrimidin-5-yl)-2-methylbut-3-yn-2-ol

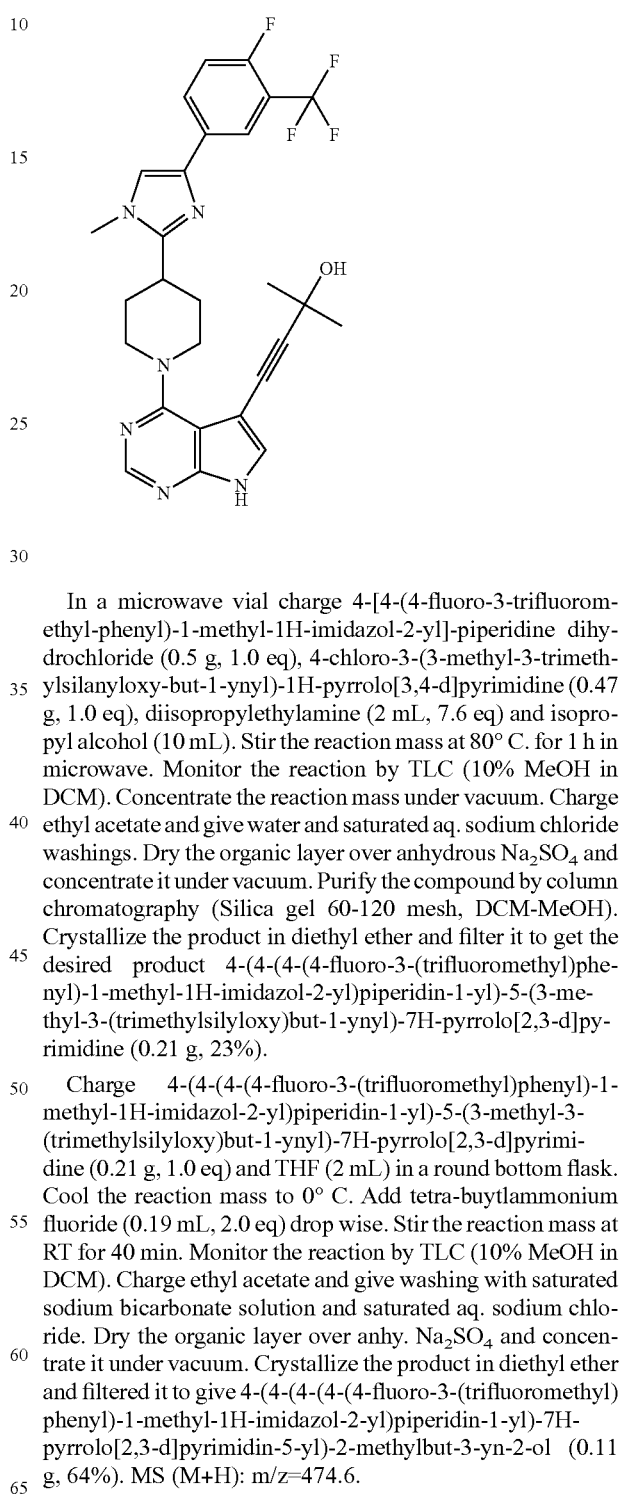

In a microwave vial charge 4-[4-(4-fluoro-3-trifluoromethyl-phenyl)-1-methyl-1H-imidazol-2-yl]-piperidine dihydrochloride (0.5 g, 1.0 eq), 4-chloro-3-(3-methyl-3-trimethylsilanyloxy-but-1-ynyl)-1H-pyrrolo[3,4-d]pyrimidine (0.47 g, 1.0 eq), diisopropylethylamine (2 mL, 7.6 eq) and isopropyl alcohol (10 mL). Stir the reaction mass at 80° C. for 1 h in microwave. Monitor the reaction by TLC (10% MeOH in DCM). Concentrate the reaction mass under vacuum. Charge ethyl acetate and give water and saturated aq. sodium chloride washings. Dry the organic layer over anhydrous Na$_2$SO$_4$ and concentrate it under vacuum. Purify the compound by column chromatography (Silica gel 60-120 mesh, DCM-MeOH). Crystallize the product in diethyl ether and filter it to get the desired product 4-(4-(4-(4-fluoro-3-(trifluoromethyl)phenyl)-1-methyl-1H-imidazol-2-yl)piperidin-1-yl)-5-(3-methyl-3-(trimethylsilyloxy)but-1-ynyl)-7H-pyrrolo[2,3-d]pyrimidine (0.21 g, 23%).

Charge 4-(4-(4-(4-fluoro-3-(trifluoromethyl)phenyl)-1-methyl-1H-imidazol-2-yl)piperidin-1-yl)-5-(3-methyl-3-(trimethylsilyloxy)but-1-ynyl)-7H-pyrrolo[2,3-d]pyrimidine (0.21 g, 1.0 eq) and THF (2 mL) in a round bottom flask. Cool the reaction mass to 0° C. Add tetra-buytlammonium fluoride (0.19 mL, 2.0 eq) drop wise. Stir the reaction mass at RT for 40 min. Monitor the reaction by TLC (10% MeOH in DCM). Charge ethyl acetate and give washing with saturated sodium bicarbonate solution and saturated aq. sodium chloride. Dry the organic layer over anhy. Na$_2$SO$_4$ and concentrate it under vacuum. Crystallize the product in diethyl ether and filtered it to give 4-(4-(4-(4-(4-fluoro-3-(trifluoromethyl)phenyl)-1-methyl-1H-imidazol-2-yl)piperidin-1-yl)-7H-pyrrolo[2,3-d]pyrimidin-5-yl)-2-methylbut-3-yn-2-ol (0.11 g, 64%). MS (M+H): m/z=474.6.

The following compounds may be prepared essentially as described in Example 53-E.

| Example | Compound | Physical Data |
|---|---|---|
| 53-F | 4-(4-(4-(4-(3,4-difluorophenyl)-1-methyl-1H-imidazol-2-yl)piperidin-1-yl)-7H-pyrrolo[2,3-d]pyrimidin-5-yl)-2-methylbut-3-yn-2-ol | MS (M + H): m/z = 475.6 |
| 53-G | 3-(4-(4-(4-(3,4-difluorophenyl)-1-methyl-1H-imidazol-2-yl)piperidin-1-yl)-7H-pyrrolo[2,3-d]pyrimidin-5-yl)prop-2-yn-1-ol | MS (M + H): m/z = 449.4 |
| 53-H | 3-(4-(4-(1-methyl-4-(3-(trifluoromethyl)phenyl)-1H-imidazol-2-yl)piperidin-1-yl)-7H-pyrrolo[2,3-d]pyrimidin-5-yl)prop-2-yn-1-ol | MS (M + H): m/z = 481.4 |
| 53-I | 5-Ethynyl-4-{4-[1-methyl-4-(3-trifluoromethyl-phenyl)-1H-imidazol-2-yl]-piperidin-1-yl}-7H-pyrrolo[2,3-d]pyrimidine (heat in sealed tube 100° C. overnight, Et₃N, deprotect with TBAF) | MS (M + H): m/z = 451 |
| 53-J | 4-{4-[4-(3,4-Difluoro-phenyl)-1-methyl-1H-imidazol-2-yl]-piperidin-1-yl}-5-ethynyl-7H-pyrrolo[2,3-d]pyrimidine (heat in sealed tube 100° C. overnight, Et₃N, deprotect with TBAF) | MS (M + H): m/z = 419 |
| 53-K | 5-Ethynyl-4-{4-[4-(4-fluoro-3-trifluoromethyl-phenyl)-1-methyl-1H-imidazol-2-yl]-piperidin-1-yl}-7H-pyrrolo[2,3-d]pyrimidine (heat in sealed tube 100° C. overnight, Et₃N, deprotect with TBAF) | MS (M + H): m/z = 469 |

EXAMPLE 54

4-{4-[4-(3-Trifluoromethyl-phenyl)-1H-imidazol-2-yl]-piperidin-1-yl}-1H-pyrazolo-[3,4-d]pyrimidine hydrochloride

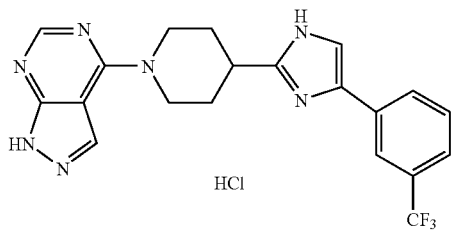

To a 22 L 4-necked round bottom flask (fitted with addition funnel, nitrogen blanket, condenser, scrubber and mechanical stirrer) add: 3-trifluoromethyl-acetophenone (1500 g, 1.00 equiv; 7.97 moles) and dichloromethane (7.5 L). Stir the resulting clear, colorless solution at room temperature while adding a solution of bromine (1274 g; 1.00 equiv; 7.97 moles) in dichloromethane at room temperature via addition funnel over 4 hours. Quench the reaction by slow addition of saturated aqueous NaHCO₃ (2000 mL), controlling the temperature by ice bath to less than 25° C. Separate the phases and wash the organic layer with saturated aqueous sodium chloride (2000 mL), then dry the solution over sodium sulfate, filter and concentrate to a clear colorless oil. Purify this crude oil by silica gel chromatography (step gradient, 20% to 50% CH₂Cl₂ in heptane) to afford 2-Bromo-1-(3-trifluoromethyl-phenyl)-ethanone (1667 g, 6.24 mol, 78%) as a clear, colorless oil.

Charge 2-bromo-1-[3(trifluoromethyl)phenyl]-1-ethanone (1664.7 g; 1.00 equiv; 6.23 moles) and tetrahydrofuran (7500 mL) to a 12 L 3-necked round bottom flask (fitted with water-cooled condenser, nitrogen blanket, mechanical stirrer and cooling bath. Charge sodium azide (425.6 g; 1.05 equiv; 6.55 moles) in one portion. Rinse into the flask with water (135 mL). Stir the pale yellow slurry at RT under nitrogen. After 6 hours, add water (260 mL) and continue to stir overnight. Filter the resulting orange slurry over a thin pad of Celite® and rinse with THF (1 L). Divide the resulting solution into two equal portions (5146.5 g each). Charge two identical 22 L 3-necked round bottom flask (fitted with addition funnel, water-cooled condenser, nitrogen blanket, mechanical stirrer and cooling bath) with triphenylphosphine (889 g, 3.43 mol, 1.1 eq), p-toluenesulfonic acid monohydrate (1304 g, 6.86 mol, 2.2 eq) and THF (5.6 L). Add the two portions of intermediate mixture via addition funnels to the individual flasks over four hours, controlling the foaming from nitrogen evolution by addition rate and the temperature by use of an ice bath. On completion of addition stir the slurry at ambient temperature for two hours, then filter solids from both reactors onto the same filter. Wash both flasks and the combined cake with a total THF (4 L). Dry in a vacuum oven at 40° C. overnight to afford (2-Amino-1-(3-trifluoromethyl-phenyl)-ethanone)-, p-toluene sulfonate (1:1) as a white, crystalline solid (2340 g, 6.23 mol, 72%).

Charge (2-Amino-1-(3-trifluoromethyl-phenyl)-ethanone)-, p-toluene sulfonate (1:1) (913 g, 2.43 mol) and 1-tert-Butoxycarbonylisonipecotic acid (623 g, 2.73 mol, 1.12 eq) along with THF (2.75 L) and EtOAc (5.5 L) and cool to 0-5° C. Add 1.2 equivalents of propylphosphonic anhydride (T3P) (1.2 eq, 2.91 mol, 1.512 L of a 50% solution in EtOAc) and maintain the reaction temperature at 0-5° C. during addition. Stir for 10 min, then add N-methylmorpholine (566 g, 5.6 mol, 2.3 eq) holding the temperature below 5° C. during addition. Warm the reaction to room temperature and after 10 hours, cool in an ice bath and add water (7.3 L). Separate the layers and wash the aqueous layer with EtOAc (2.75 L). Combine the organic layers and wash with 0.5M aqueous sodium bicarbonate solution (2.75 L). Wash the organic layer with saturated aqueous sodium chloride (2.75 L), then treat the resulting organic layer with sodium sulfate and filter. Remove the solvent via distillation down to ~4.6 L. Add back heptane (11 L) while removing solvent via distillation until the final volume reaches ~11 L. Cool to 50° C. and seed. Hold the resulting slurry at 50° C. for 3 h, then cool the slurry to room temperature and stir for 2 h. Filter the solids and wash the cake, first with 10% EtOAc in heptane (2 L) then with heptane (2 L). After drying in a vacuum oven at 60° C. for 3 h, 800 g (79%) of 4-[2-Oxo-2-(3-trifluoromethyl-phenyl)-ethylcarbamoyl]-piperidine-1-carboxylic acid tert-butyl ester is obtained as a white solid.

Prepare a solution of 4-[2-Oxo-2-(3-trifluoromethyl-phenyl)-ethylcarbamoyl]-piperidine-1-carboxylic acid tert-butyl ester (773.3 g; 1.00 equiv; 1.87 moles) in methanol (2300 mL). Prepare a solution of ammonium acetate (755.08 g; 9.80 moles) in methanol (3500 mL). Pump the two solutions at a 5:1 mol ratio of ammonium acetate to 4-[2-Oxo-2-(3-trifluoromethyl-phenyl)-ethylcarbamoyl]-piperidine-1-carboxylic acid tert-butyl ester, with a residence time of 45 minutes. Combine the two streams in a tee at room temperature and then allow to flow into a thermal tube reactor with the oven temperature at 170° C. for 5 hours. Combine all of the collected product solution and concentrate under reduced pressure, then solvent exchange into 3500 mL of n-BuOH. Wash this solution with a mixture of 3000 mL of saturated aqueous NaHCO$_3$ and 1000 mL water. Wash again with saturated aqueous sodium chloride (3000 mL), followed by azeotropic drying by distillation of 1 L of n-BuOH (45° C. bath temp). Filter the solids that precipitate during distillation. Charge the filtrate to a 5 L 4-neck flask in a cooling bath. Bubble anhydrous HCl gas slowly into the solution, controlling the temperature <55° C. with ice water bath. On completion of reaction add Heptane (4000 mL) slowly via addition funnel, then cool the resulting slurry to <5° C. in an ice bath, hold for 15 min. Filter the solids and wash the cake with heptane (2×600 mL). Dry solids in 40° C. vacuum oven to afford (4-[4-(3-Trifluoromethyl-phenyl)-1H-imidazol-2-yl]-piperidine)-, Hydrochloride (1:1) as a white solid (619.1 g, 1.87 mol, 92%).

Charge 4-Chloro-1H-pyrazolo[3,4-d]pyrimidine (93.3 g; 1.00 equiv; 603.66 mmoles; 93.30 g), (4-[4-(3-Trifluoromethyl-phenyl)-1H-imidazol-2-yl]-piperidine)-, Hydrochloride (1:1) (200.1 g; 1.00 equiv; 603.13 mmoles), and Methanol (1800 mL) to a 5000 mL 4-necked round bottom flask (fitted with nitrogen blanket, rubber septum, mechanical stirrer, heating mantle, condenser and thermocouple probe). Add Triethylamine (280 mL; 2.01 moles) via addition funnel over approximately 15 min. Heat the resulting clear orange solution to 50° C. and hold at 50° C. for 15 min. When reaction is deemed complete by HPLC, add Water (2000 mL) via an addition funnel at 50° C. Add seed crystals during this water addition and the product crystallizes. On completion of addition, heat the slurry to reflux for 1 hour. Cool to room temperature then filter and wash solids with 20% MeOH in water (2×250 mL). Dry the solids in a vacuum oven at 45° C. overnight to afford 4-{4-[4-(3-Trifluoromethyl-phenyl)-1H-imidazol-2-yl]-piperidin-1-yl}-1H-pyrazolo[3,4-d]pyrimidine as a tan solid (211.5 g, 0.603 mol, 85%).

m.p.=281° C.; MS m/z=414 [M+H]

4 Charge 4-{4-[4-(3-Trifluoromethyl-phenyl)-1H-imidazol-2-yl]-piperidin-1-yl}-1H-pyrazolo[3,4-d]pyrimidine (442.9 g, 1.07 mol) along with IPA (4.43 L) and stir the resulting slurry at RT. Slowly add HCl (214 mL of a 5M aqueous solution, 1.07 mol, 1.0 eq) and heat to 50° C. Stir for 30 minutes and add acetone (4.43 L) and continue heating for 4 h. Cool to 15° C. for 2 hr then filter the solid. Wash the filter cake with acetone (800 mL) and dry resulting solid in vacuum oven at 60° C. for 3 h to afford the title compound (458 g, 94%) as a tan to off-white solid. M.p.=306° C.; MS (ES): m/z=414 [M+H]

EXAMPLE 55

4-{4-[4-(4-Fluoro-3-trifluoromethyl-phenyl)-1-methyl-1H-imidazol-2-yl]-piperidin-1-yl}-1H-pyrazolo[3,4-d]pyrimidine hydrochloride

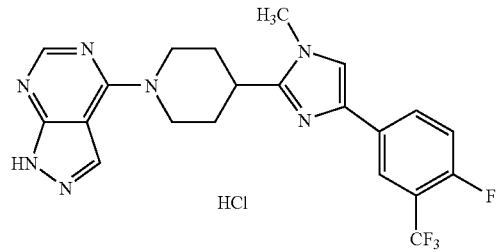

Add methenamine (1.10 equiv; 231.55 mmoles; 32.46 g) to a solution of 4-fluoro-3-(trifluoromethyl)phenacyl bromide (60.00 g 1.00 equiv; 210.50 mmoles) in ethyl acetate (450 mL; 4.60 moles). Stir the mixture at room temperature overnight. Remove the solvent in vacuo and triturate the solid in MTBE. Filter and dry under reduced pressure. Add ethanol (450 mL; 7.73 moles), followed by hydrogen chloride (150 mL; 8.30 equiv; 1.75 moles) and stir the mixture at room temperature overnight. Remove the solvent in vacuo and dry the solid in vacuo at 50° C. for a week to obtain 2-Amino-1-(4-fluoro-3-trifluoromethyl-phenyl)-ethanone hydrochloride (54.23 g; 100% yield) as a white solid.

Add N-methylmorpholine (3 equiv; 631.52 mmoles; 69.66 mL) to a solution of Piperidine-1,4-dicarboxylic acid mono-tert-butyl ester (1.20 equiv; 252.61 mmoles; 57.92 g) in THF (400 mL). Cool the mixture to −10° C. with a dry ice-acetone bath. Add isobutyl chloroformate (1.1 equiv; 231.56 mmoles; 30.26 mL) dropwise while maintaining the temperature below −5° C. After 30 min at −5°–10° C., add 2-amino-1-(4-fluoro-3-trifluoromethyl-phenyl)-ethanone hydrochloride (54.23 g; 1.00 equiv; 210.51 mmoles) suspended in THF (300 mL) and stir the mixture in the bath at −5° C. for 20 min. Stir for 1 hour at room temperature. Add water and EtOAc, then wash the organic layer with water and saturated aqueous sodium chloride. Dry over MgSO$_4$, filter and remove solvent in vacuo. Suspend the crude in MTBE and stir for 2 hours. Filter the solid and dry in vacuo to give 1-[2-(4-Fluoro-3-trifluoromethyl-phenyl)-2-oxo-ethylcarbamoyl]-piperidine-4-carboxylic acid tert-butyl ester (64.44 g; 70.79% yield).

Add ammonium acetate (15 equiv; 1.02 moles; 78.61 g) to a solution of 1-[2-(4-fluoro-3-trifluoromethyl-phenyl)-2-oxo-ethylcarbamoyl]-piperidine-4-carboxylic acid tert-butyl ester (29.4 g; 1.00 equiv; 67.99 mmoles) in 1-butanol (150 mL; 1.64 moles), then add triethylamine (1 equiv; 67.99 mmoles; 9.48 mL). Stir the mixture at 160° C. in a sealed tube for 3 h. Add EtOAC and water, then wash the organic layer with more water and saturated aqueous sodium chloride and concentrated in vacuo. Triturate the crude in MTBE, filter and dry under reduced pressure to give 4-[4-(4-Fluoro-3-trifluoromethyl-phenyl)-1H-imidazol-2-yl]-piperidine-1-carboxylic acid tert-butyl ester (18.23 g; 44.10 mmoles, 64.86% yield) as a white solid.

Add 4-[4-(4-Fluoro-3-trifluoromethyl-phenyl)-1H-imidazol-2-yl]-piperidine-1-carboxylic acid tert-butyl ester (16.03 g; 1.00 equiv; 38.77 mmoles) in 40 mL of dimethyl sulfoxide to a solution of potassium hydroxide (1.5 equiv; 58.16 mmoles; 3.26 g) in 200 mL of dimethyl sulfoxide. After 5 min at room temperature, add methyl iodide (1.1 equiv; 42.65 mmoles; 2.66 mL) in one portion. Stir at room temperature for two hours, then pour the mixture into ice water. Filter the solid, wash with water, and dry under reduced pressure. Triturate the solid in hot heptane, filter and dried under reduced pressure to give 4-[4-(4-Fluoro-3-trifluoromethyl-phenyl)-1-methyl-1H-imidazol-2-yl]-piperidine-1-carboxylic acid tert-butyl ester (8.7 g; 52.49% yield) as a white solid.

Add hydrogen chloride (4.00 equiv; 81.41 mmoles; 20.35 mL) to a solution of 4-[4-(4-Fluoro-3-trifluoromethyl-phenyl)-1-methyl-1H-imidazol-2-yl]-piperidine-1-carboxylic acid tert-butyl ester (8.7 g; 1.00 equiv; 20.35 mmoles) in dichloromethane (101.77 mL), at room temperature. Stir the solution at room temperature for 1 hour. Remove the solvent under reduced pressure, and dissolve the crude in isopropyl alcohol (101.77 mL). Add 4-chloro-1H-pyrazolo[3,4-d]pyrimidine (1.65 equiv; 33.58 mmoles; 5.19 g) and triethylamine (10 equiv; 203.54 mmoles; 28.37 mL). Stir the mixture at reflux for 1 hour. Remove the solvent under reduced pressure and triturate the crude in water overnight. Filter the solid and triturated in hot acetonitrile, filter and dry in vacuo. 4-{4-[5-(4-Fluoro-3-trifluoromethyl-phenyl)-3-methyl-1H-imidazol-2-yl]-piperidin-1-yl}-1H-pyrazolo[3,4-d]pyrimidine (8.42 g; 18.86 mmoles; 92.66% yield) is obtained as a light yellow solid.

Add hydrogen chloride (1.1 equiv; 18.52 mmoles; 4.63 mL) to a suspension of 4-{4-[4-(4-fluoro-3-trifluoromethyl-phenyl)-1-methyl-1H-imidazol-2-yl]-piperidin-1-yl}-1H-pyrazolo[3,4-d]pyrimidine (7.5 g; 1.00 equiv; 16.84 mmoles) in dichloromethane (50 mL), and stir the mixture for 1 hour at room temperature. Remove the solvent in vacuo, and triturate the crude in MTBE for 1 hour. Filter the solid and dry in vacuo overnight to give 4-{4-[4-(4-Fluoro-3-trifluoromethyl-phenyl)-3-methyl-1H-imidazol-2-yl]-piperidin-1-yl}-1H-pyrazolo[3,4-d]pyrimidine hydrochloride (7.99 g; 16.58 mmoles; 98.47% yield) as a white solid. $^1$H-NMR (300 MHz, DMSO): δ14.01-13.99 (m, 1H), 8.57-8.54 (m, 2H), 8.26-8.19 (m, 3H), 7.72-7.63 (m, 1H), 5.23-5.20 (m, 2H), 3.89 (s, 3H), 3.41 (m, 2H), 2.15-2.07 (m, 3H), 1.10 (s, 2H).

EXAMPLE 56

Crystalline 4-{4-[4-(3-Trifluoromethyl-phenyl)-1H-imidazol-2-yl]-piperidin-1-yl}-1H-pyrazolo[3,4-d]pyrimidine hydrochloride Suspend 4-{4-[4-(3-Trifluoromethyl-phenyl)-1H-imidazol-2-yl]-piperidin-1-yl}-1H-pyrazolo[3,4-d]pyrimidine (134 mg) in acetone (2 mL). Heat the suspension to 77° C., then add methanol (1 mL). Add 0.25M HCl (1.28 mL) to the solution and cool slowly. Add heptane (2 mL) followed by acetone (6 mL). Allow evaporation overnight at room temperature. Add acetone (3 mL) to the resulting oil and slurry the resulting white solid in acetone for 4 hours. Filter the suspension and air-dry to provide 98 mg, dry in vacuum oven at 45° C. under vacuum. The form has endothermic onset at 294° C.

X-ray powder diffraction analysis is performed with a D4 Endeaver diffractometer, equipped with a CuKα source (λ=1.54056 Å) operating at 40 kV and 50 mA. The sample is scanned from 4° to 40° in 2θ, with a step size of 0.009° in 2θ and a scan rate of ≧1.5 sec per step. Sample displacement error is corrected using the NIST standard SRM675 (standard peak at 8.8° in 2θ).

| Angle 2-theta (±0.1°) | Intensity % |
| --- | --- |
| 7.1 | 39.5 |
| 10.7 | 9.1 |
| 12.8 | 13.3 |
| 13.0 | 14.8 |
| 13.5 | 15.1 |
| 15.0 | 9.3 |
| 16.1 | 28.1 |
| 16.3 | 20.3 |
| 17.2 | 24.0 |
| 18.7 | 20.6 |
| 18.9 | 9.8 |
| 19.4 | 17.3 |
| 19.8 | 30.7 |
| 20.4 | 16.0 |
| 21.7 | 100.0 |
| 22.6 | 44.1 |
| 22.7 | 30.4 |
| 23.1 | 17.5 |
| 24.6 | 34.9 |
| 26.0 | 7.5 |
| 27.0 | 6.3 |
| 29.7 | 11.0 |
| 30.3 | 7.2 |

The present invention provides crystalline 4-{4-[4-(3-Trifluoromethyl-phenyl)-1H-imidazol-2-yl]-piperidin-1-yl}-1H-pyrazolo[3,4-d]pyrimidine hydrochloride characterized by at least one peak in the x-ray pattern at 2θ diffraction angle of 7.1°±0.1 or 21.7°±0.1. The present invention also provides a pharmaceutical formulation comprising crystalline 4-{4-[4-(3-Trifluoromethyl-phenyl)-1H-imidazol-2-yl]-piperidin-1-yl}-1H-pyrazolo[3,4-d]pyrimidine hydrochloride characterized by at least one peak in the x-ray pattern at 2θ diffraction angle of 7.1°±0.1 or 21.7°±0.1. The present invention further provides the use of crystalline 4-{4-[4-(3-Trifluoromethyl-phenyl)-1H-imidazol-2-yl]-piperidin-1-yl}-1H-pyrazolo[3,4-d]pyrimidine hydrochloride characterized by at least one peak in the x-ray pattern at 2θ diffraction angle of 7.1°±0.1 or 21.7°±0.1 for the manufacture of a medicament for the inhibition of angiogenesis or treatment of adenocarcinoma of the colon.

General Procedure for the Preparation of Salts and Crystals

A master plate is prepared with 250 μL of the free base of the subject compound in methanol (0.1M) added to all wells set in a 96 well format. An array of acids is dispensed to each well in stoichiometric molar equivalents. The solvents are evaporated from all 96 wells using a Genevac Series II evaporator leaving solid residues or oils in the master plate. An array of solvents is dispensed to each one of these wells through a sealing gasket and then heated to 55° C. with stirring and allowed to equilibrate for 60-90 minutes at about 55° C. Each sample is then filtered hot and transferred to corresponding wells in an evaporation plate, a precipitation plate, and a cooling plate. The evaporation plate is prepared by transferring 200 μL of the filtrate from the master plate using 55° C. heated syringes to the open well titer plate and is then allowed to evaporate to dryness over night at room temperature and ambient humidity. The precipitation plate is prepared by adding 100 μL of the filtrate from the master plate using 55° C. heated syringes to a gasket-sealed 96 well titer plate where each well contains an anti-solvent of 200 μL of heptane or water. After equilibrating for a period of nine hours at room temperature, the excess solution is wicked away using pre-cut Whatman filter paper. The cooling plate is prepared by transferring 200 μL of the filtrate from the master plate to individual wells using 55° C. heated syringes in a gasket-sealed titer plate, and cooling exponentially from 55° C. to 10° C. over a period of 8 hours. Photomicrographs are collected on the material in each well in the 96 well plates using a Zeiss Axiovert 200M inverted incident-light microscope with a 2.5× objective. If the material is crystalline, it exhibits birefringence that is displayed as white against a dark background. Amorphous solids or oils appear dark or as opaque droplets or rings.

EXAMPLE 57

4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate Cool a solution of 4-fluoro-3-(trifluoromethyl)phenacyl bromide (93% pure by HPLC, 1000 g; 3.51 moles) and tetrahydrofuran (5 L) to <5° C. in an ice bath. Add a solution of sodium azide (239 g; 3.68 moles, 1.05 eq) in water (800 mL) drop wise over one hour at <5° C. After stirring at <5° C. for one hour, separate and discard the aqueous layer. While still cold, add the organic layer slowly over 3 hours to a solution of triphenylphosphine (920.2 g, 3.51 moles, 1.0 eq), p-toluenesulfonic acid monohydrate (1335 g, 7.02 moles, 2.0 eq), and THF (5 L). Maintain the temperature at <15° C. throughout this addition and solids precipitate during the addition.

Stir the reaction mixture at <20° C. for 2 hours and then filter the solid, wash with THF (3×2 L), and dry at 50° C. under vacuum to give 1167.4 g (85%, 92% corrected for starting material purity) of 2-amino-1-(4-fluoro-3-trifluoromethyl-phenyl)-ethanone p-toluenesulfonate as a white crystalline solid.

Combine 2-amino-1-(4-fluoro-3-trifluoromethyl-phenyl)-ethanone p-toluenesulfonate (1133 g; 2.88 moles), 1-(tert-butoxycarbonyl)piperidine-4-carboxylic acid (795 g; 3.47 moles, 1.20 eq), tetrahydrofuran (3450 mL), and ethyl acetate (7500 mL) to form a thin white slurry. Cool the slurry to <5° C. in ice bath and add 2-propanephosphonic acid anhydride ($T_3P$) (50% solution in EtOAc) (2385 g; 3.75 moles, 1.3 eq). Then add N-methylmorpholine (795 mL; 7.21 moles, 2.5 eq) over 1 hour, maintaining the temperature <10° C. Warm the resulting slurry to ambient temperature and stirr for 2 hours.

Quench the reaction by addition of water. Separate the organic phase, then wash with aqueous $NaHCO_3$, aqueous NaCl. Warm the organic phase to 50° C. on a rotary evaporator and add n-heptane. Distill solvent under vacuum until the final slurry volume is approximately 5 L. Cool the slurry to room temperature and filter the solids, wash with n-heptane (2×1 L) and then dry in a vacuum oven at 50° C. overnight, resulting in 1-[2-(4-fluoro-3-trifluoromethyl-phenyl)-2-oxo-ethylcarbamoyl]-piperidine-4-carboxylic acid tert-butyl ester (1124.8 g, 90%) as a white solid.

Combine 1-[2-(4-fluoro-3-trifluoromethyl-phenyl)-2-oxo-ethylcarbamoyl]-piperidine-4-carboxylic acid tert-butyl ester (100 g, 231 mmoles), ammonium acetate (178.3 g; 2.31 moles, 10 eq), and methanol (1000 mL). The reactor used for this transformation is a coiled 1/16" I.D. stainless steel tube (total internal volume of tubing in oven is 541 mol). Heat the reactor in an oven to 140° C. Control the back pressure in this tube at 250 psig by a regulator to allow super-heating of the solution above its normal boiling point. Pump the solution prepared above continuously through the heated tube under pressure at 6.01 mL/min (affording a total residence time in the heated tube of 90 minutes). As the solution exits the oven, cool it back to 20° C. in a tube-in-tube heat exchanger. Once the entire solution process through the reactor (8 hours total processing time), concentrate the resulting orange solution under vacuum at 30° C. to a total volume of 600 mL. Add acetonitrile (200 mL) and heat the solution to 50° C. Add water (700 mL) drop wise with seeding over 2 hours to crystallize the product. Cool the resulting slurry to 20° C. and filter the solid, then wash with 20% MeOH in water (2×200 mL). Dry the resulting solid under vacuum at 50° C. Re-slurry the solid in acetonitrile (200 mL) at 50° C. Cool the slurry to ambient temperature, filter the solid and wash with acetonitrile (100 mL) to afford 4-[4-(4-fluoro-3-trifluoromethyl-phenyl)-1H-imidazol-2-yl]-piperidine-1-carboxylic acid tert-butyl ester (54.43 g, 132 mmoles, 57%) as an off white solid.

Dissolve 4-[4-(4-fluoro-3-trifluoromethyl-phenyl)-1H-imidazol-2-yl]-piperidine-1-carboxylic acid tert-butyl ester (80.02 g, 183.69 mmoles) in dimethyl sulfoxide (1060 mL). Add KOH (18.47 g; 279.82 mmoles; 1.5 eq) in one portion. Add methyl iodide (27.74 g; 193.48 mmoles, 1.05 eq) over 30 minutes at 25° C. Stir the solution at 25° C. for 1 hour. Add a mixture of 4-[4-(4-fluoro-3-trifluoromethyl-phenyl)-1-methyl-1H-imidazol-2-yl]-piperidine-1-carboxylic acid tert-butyl ester seed crystals (0.17 g) and water (80 mL) over 5 minutes to the solution. Stir the resulting thin slurry at 25° C. for 30 minutes. Add additional water (240.73 mL) over 30 minutes at 25° C. Filter The solid and wash with 20% DMSO in water (2×120 mL) and then water (120 mL). Dry the solid under vacuum at 60° C. Dissolve the resulting dried solids in ethanol (480 mL) at 50° C. Add water (240 mL) over 5 minutes. Then add 4-[4-(4-fluoro-3-trifluoromethyl-phenyl)-1-methyl-1H-imidazol-2-yl]-piperidine-1-carboxylic acid tert-butyl ester seed (0.038 g) and more water (240 mL) over 30 minutes. Cool the resulting slurry to 25° C. over 2 hours. Filter the solids and wash the cake with 20% EtOH in water. Dry the solid under vacuum at 60° C. affording 4-[4-(4-fluoro-3-trifluoromethyl-phenyl)-1-methyl-1H-imidazol-2-yl]-piperidine-1-carboxylic acid tert-butyl ester (72.36 g, 92%) as a white solid.

Prepare an anhydrous HCl solution by slow addition of acetyl chloride (193.14 mL; 2.71 moles, 4.00 eq) to methanol (1160 mL) over 45 minutes at <5° C. Add the resulting solution to a separate flask containing a solution of 4-[4-(4-fluoro-3-trifluoromethyl-phenyl)-1-methyl-1H-imidazol-2-yl]-piperidine-1-carboxylic acid tert-butyl ester (290 g; 678.46 mmoles) in methanol (2320 mL) over 90 minutes at 20° C. Stir the reaction mixture at 20° C. overnight. Concentrate the reaction mixture under vacuum at 30° C. Add dimethyl sulfoxide (1080 mL; 15.20 moles; 1.08 L; 1.19 kg) and the distillation continues until the internal temperature reaches 50° C. at a pressure of 20 mm Hg. Add DMSO until the total volume is 2030 mL. Then add triethylamine (473 mL; 3.39 moles, 5 eq) via addition funnel over 30 minutes. Charge solid 4-chloro-1H-pyrazolo[3,4-d]pyrimidine (110.29 g; 713.58 mmoles, 1.05 eq) in equal portions equally spaced over 30 minutes. Stir the resulting slurry at 20° C. overnight. Heat the slurry to 80° C. Add water (229 mL) to afford a clear solution. Seed the reaction and add more water (1273 mL) slowly over 4 hours to fully crystallize the product. Cool the slurry to 50° C. and filter the solid. Wash the cake with 30% water in DMSO (2×290 mL), then water (290 mL). Dry the solids under vacuum at 60° C. to afford 4-{4-[4-(4-fluoro-3-trifluoromethyl-phenyl)-1-methyl-1H-imidazol-2-yl]-piperidin-1-yl}-1H-pyrazolo[3,4-d]pyrimidine (301 g, 99%) as an off white solid.

Dissolve 4-{4-[4-(4-fluoro-3-trifluoromethyl-phenyl)-1-methyl-1H-imidazol-2-yl]-piperidin-1-yl}-1H-pyrazolo[3,4-d]pyrimidine (20 g, 44.9 mmoles) in a 20:1 $H_2O$:acetone mixture (360 mL). Add a solution of p-toluenesulfonic acid monohydrate (10.25 g, 53.9 mmoles, 1.2 eq) in a 20:1 H$_2$O:acetone mixture (40 mL) to the reaction over 20 minutes at 20° C. Heat the reaction mixture to 55° C., hold for 1 hour, then cool to 25° C. over 1 hour. Filter the solid and wash the cake with water (40 mL). Drying under vacuum at 50° C. affords 4-{4-[4-(4-fluoro-3-trifluoromethyl-phenyl)-1-methyl-1H-imidazol-2-yl]-piperidin-1-yl}-1H-pyrazolo[3,4-d]pyrimidine p-toluenesulfonate (23.9 g, 86%) as a white solid.

EXAMPLE 58

Crystalline 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate To a 1-L round bottom flask with overhead stirrer charge with 60.12 g of 4-{4-[4-(4-Fluoro-3-trifluoromethyl-phenyl)-1-methyl-1H-imidazol-2-yl]-piperidin-1-yl}-1H-pyrazolo[3,4-d]pyrimidine, followed by 250 mL of 5% aq. MeOH. Stir the resulting slurry and add p-toluenesulfonic acid monohydrate (26.88 g) followed by a rinse forward with the remaining 50 mL of 5% aq. MeOH. Stir the resulting slurry and cool the crystals to 5° C. After 1 h at 5° C., stop stirring and filter the slurry on a Buchner funnel. Rinse the flask out with 75 mL of cold 5% aq. MeOH and use this rinse to wash the filter cake. Transfer the solids to a weighing dish and dry at 50° C. in vacuo all day and all night, with a slow air bleed. The final weight is 71.44 g.

X-ray powder diffraction analysis is performed with a D4 Endeaver diffractometer, equipped with a CuKa source (λ=1.54056 Å) operating at 40 kV and 50 mA. The sample is scanned from 4° to 40° in 2θ, with a step size of 0.009 in 2θ and a scan rate of ≧1.5 sec per step.

| Angle 2-theta (±0.1°) | Intensity % |
|---|---|
| 6.826 | 12 |
| 10.256 | 24 |
| 12.984 | 24 |
| 13.131 | 61 |
| 13.431 | 25 |
| 13.688 | 100 |
| 14.062 | 24 |
| 15.745 | 6 |
| 17.121 | 15 |
| 18.599 | 5 |
| 18.919 | 21 |
| 19.38 | 29 |
| 20.603 | 14 |
| 21.661 | 6 |
| 21.962 | 14 |
| 22.108 | 9 |
| 23.485 | 14 |
| 23.615 | 17 |
| 23.866 | 22 |
| 24.024 | 20 |
| 24.667 | 11 |
| 24.795 | 11 |
| 25.029 | 8 |
| 25.552 | 9 |
| 26.234 | 5 |
| 26.556 | 10 |
| 27.031 | 6 |
| 27.693 | 11 |
| 27.97 | 5 |
| 28.352 | 6 |
| 28.428 | 5 |
| 38.232 | 5 |

The present invention provides crystalline 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate characterized by at least one peak in the x-ray pattern at 2θ diffraction angle of 13.7°±0.1 or 10.3°±0.1. The present invention also provides a pharmaceutical formulation comprising crystalline 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate characterized by at least one peak in the x-ray pattern at 2θ diffraction angle of 13.7°±0.1 or 10.3°±0.1. The present invention further provides the use of crystalline 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate characterized by at least one peak in the x-ray pattern at 2θ diffraction angle of 13.7°±0.1 or 10.3°±0.1 for the manufacture of a medicament for the inhibition of angiogenesis or treatment of adenocarcinoma of the colon.

Inhibition of p70S6 Kinase

P70 S6 kinase (T412E) from Upstate USA, Inc. (Charlottesville, Va.) is preincubated with 10 concentrations of compound in a 15 µL volume for 30 min at room temperature in 96-well plates. PKA, PKC, MAPKAP-K1 Substrate from AnaSpec (San Jose, Calif.) and gamma $^{33}$P-ATP from PerkinElmer (Waltham, Mass.) is added to initiate the reaction which is allowed to proceed for 60 minutes at room temperature in a final 25 µL volume under the following conditions: 10 mM HEPES pH 7.5, 10 mM MgCl$_2$, 1.0 mM DTT, 0.082 mM EGTA, 0.005% TRITON X-100™, 25 µM, 25 µM ATP, 40 µCi/mL, 4 µM substrate, and 5 nM enzyme. Reactions are terminated with 75 µL 10% H3PO4 and 85 µL of quenched reaction mix is transferred to a phosphocellulose filter plate (Millipore #MAPHN0B50) and washed with 0.5% H$_3$PO$_4$ using a vacuum manifold. 100 µL of Microscint 20 (Packard #60113621) is added to each well and plates with liner are counted using a Wallac Beta Counter. Relative IC$_{50}$ values are calculated by non-linear four parameter fitting. The exemplified compounds were tested essentially as described above and were found to have IC$_{50}$ values less than or equal to 0.75 µM. The following compounds were tested essentially as described above and were found to have the following activity:

| EXAMPLE | IC$_{50}$ (µM) |
|---|---|
| 5 | 0.0294 |
| 7 | 0.0103 |
| 8 | 0.00758 |
| 10 | 0.00379 |
| 57 | 0.0127 |

This demonstrates that compounds of the present invention are potent p70 S6 kinase inhibitors.

Angiogenesis Cord Formation Assay

Human neonatal dermal fibroblast cells (neo NHDF) are seeded into Parkard 96 well plate on the first day, and incubated in the 37° C. and 5% CO$_2$ incubator. Human umbilical vein endothelial cells (HUVEC) are then plated on the top of neo NHDF cells. Starting the third day, the co-culture is treated with eight-dose series of the test compound (starting with 20 µM, 1:3 serial dilution) in the presence of 20 ng/mL vascular endothelial growth factor (VEGF). The compound and VEGF are replenished every two to three days. The assay is conducted over a 12 day period. Cells are fixed by cold 70% ethanol for 30 minutes on the 12$^{th}$ day and processed for anti human CD31 immunofluorescence. Cultures are incubated with mouse anti human CD31 antibody and then stained by goat anti mouse alexa 488 secondary antibody. Cells are also stained by Hoechst to visualize the nucleus. After the staining, the cord formation is captured and quantified using Cellomics Arrayscan® VTI high content image analysis platform adopting the tube formation BioApplication. Two parameters, the cord area and angiogenesis index, are used to calculate the relative potency of the test compound in this angiogenesis assay. The compounds of Examples 5 and 10 were tested and analyzed essentially as described above.

| EXAMPLE | IC$_{50}$ (μM) |
|---|---|
| 5 | 2.92 |
| 10 | 4.78 |

This demonstrates that compounds of the present invention are useful in inhibiting angiogenesis.

Cell Assays

Cells are maintained, then typsinized and suspended in Dulbecco's modified Eagle's medium (DMEM_containing 10% fetal bovine serum (FBS), 25 mM 4-(2-hydroxyethyl)-1-piperazineethanesulfonic acid (HEPES), 1.0 mM Sodium Pyruvate and 0.1 mM Non Essential Amino Acids (NEAA). 1×10$^3$ HCT116 and 2×10$^3$ Cells may be seeded in 50 μL in 96 well plates and incubated in 5% CO$_2$ at 37° C. overnight. Compounds are prepared at desired starting concentrations and serial diluted in DMSO. 4 μL of diluted compounds are transferred in 1 mL 10% FBS DMEM to make up 2× concentrations as added 50 μL to the 50 μL in the presence of cells for dosing. The plates are incubated at 37° C. in 5% CO$_2$ for 72 hours. At the end of incubation period, 10 μL Alamar Blue is added and after 2 hours reaction the measurement is determined in CytoFluor at 530 nm excitation, 580 nm emission and Gain 45. The following compounds were tested in the following cell lines essentially as described above.

| EX-AM-PLE | U87MG IC$_{50}$ (μM) | A549 IC$_{50}$ (μM) | A2780 IC$_{50}$ (μM) | NCI-H460 IC$_{50}$ (μM) | PANC-1 IC$_{50}$ (μM) | Rat 13762 IC$_{50}$ (μM) | PC3 IC$_{50}$ (μM) | K562 IC$_{50}$ (μM) |
|---|---|---|---|---|---|---|---|---|
| 5 | 14.6 | 22 | NA | NA | NA | NA | NA | NA |
| 57 | 27.52 | 10.28 | 25.05 | 23.99 | 30.24 | 51.62 | 31.92 | 16.46 |

This indicates that the compounds of the present invention are useful in inhibiting the proliferation of these cell lines via a mechanism involving p70 S6 kinase.

Determination of p70 S6K In Vivo Target Inhibition (HCT 116)

HCT 116 human colon carcinoma cells* (5×10$^6$) are subcutaneously implanted into the flank of athymic nude mice in 0.2 mL of matrigel. Two weeks post-implantation, mice are dosed PO according to a time course, single dose/single time point, or dose response protocol for the determination of TMED$_{50}$ (threshold minimum effective dose). Tumors are flash frozen at harvest and blood is collected for the determination of parent compound plasma exposure and the calculation of TMEC$_{50}$ (threshold minimum effective concentration) in the case of dose response studies. Tumors or tissues are homogenized in XY Lysis buffer (10 μg/mL Leupeptin, 10 μg/mL Trypsin-Chymotrypsin Inhibitor, 10 μg/mL Tosyl phenylalanyl chloromethyl ketone (TPCK), 10 μg/mL Aprotinin, 60 mM Beta-Glycerol Phosphate, 1% Triton X100, 25 mM Tris pH 7.5, 2.5 mM Pyrophosphate, 150 mM NaCl, 2 mM p-tosyl-L-arginine methyl ester (TAME), 15 mM paranitrophenyl phosphate (pNPP), 5 mM Benzamidine, 1 mM Na Vanadate, 10 mM NaF, 50 μg/mL phenylmethane sulofnyl fluoride (PMSF), 1 mM DTT, 15 mM EDTA pH 8.0, 5 mM EGTA pH 8.0, 1 μM Microcystin, 1 μM Okadaic Acid, and 1 Roche Complete protease inhibitor mini-tablet per 10 mL) using Lysing Matrix A tubes (MP Biomedicals, Solon, Ohio, cat# 6910-500) and a BIO101 Thermo Savant Fast Prep FP12. Lysates are aliquoted and either assayed immediately or stored at −80° C. for later testing. In Vivo Target Inhibition of p70 S6K is measured utilizing Meso Scale Discovery (Gaithersburg, Md.) ELISA technology to assess effects of the compound on phosphorylation of the serine 240/244 site of the downstream effector S6RP. Phosphorylation of p70 S6K (T389) and Akt(S473) is also assessed using this technology in a multiplex format. In summary, 20 μg of lysate is added to a carbon electrode 96-well plate pre-spotted with the appropriate capture antibodies. The protein of interest is probed using a ruthenium labeled detection antibody. Upon the passage of current over the electrode in the presence of read buffer containing the co-reactant TPA, electro-chemiluminescence results in the generation of light which is quantified and recorded using the MSD Sector 6000 instrument. For each study, percent inhibitions are calculated relative to the vehicle control group and ANOVA analysis is performed using the JMP software package for the determination of statistical significance. The following compounds were tested essentially as described above and have the following potencies based on plasma exposure.

| EXAMPLE | IC$_{50}$ (μM) |
|---|---|
| 5 | 7.3 |
| 7 | 1.92 |
| 8 | 47.7 |
| 10 | 1.97 |

*Alternatively, U87MG cells may be used in the procedure described above.

This demonstrates the ability of compounds of the present invention to inhibit p70 S6 kinase in vivo.

Determination of p70 S6K In Vivo Efficacy

HCT 116 human colon carcinoma cells (5×10$^6$) are subcutaneously implanted into the flank of athymic nude mice in 0.2 mL of matrigel. One week post-implantation, mice are dosed PO according to the pharmacokinetics and the pharmacodynamics of the molecule to maintain 30-50% or 60-90% pS6 Inhibition over a 24 hr period. Dosing is continued for at least 21 days. Tumor volumes are measured bi-weekly to evaluate drug related tumor growth reduction utilizing standard methods. At the end of the study, tumors are flash-frozen at harvest and blood is collected for the determination of parent compound plasma exposure. The compound of Example 5 was tested essentially as described above.

| Day | Vehicle Tumor Volume[a] | 30 mg/kg PO (BID × 21) Tumor Volume[a] | 60 mg/kg PO (BID × 21) Tumor Volume[a] | 60 mg/kg PO (QD × 21) Tumor Volume[a] |
|---|---|---|---|---|
| 8  | 38.5 ± 4.1   | 36.5 ± 3.1[b]    | 28.8 ± 2.6[b]   | 30.6 ± 3.4[b]   |
| 13 | 100.9 ± 13.7 | 58.7 ± 4.8**     | 42.1 ± 6.2***   | 57.8 ± 10.7**   |
| 16 | 163.1 ± 25.7 | 90.9 ± 9.4***    | 72.1 ± 11.8***  | 85.0 ± 13.3***  |
| 20 | 287.1 ± 31.9 | 134.6 ± 13.2***  | 139.0 ± 26.4*** | 142.5 ± 18.4*** |
| 23 | 402.2 ± 43.1 | 192.7 ± 13.5***  | 188.4 ± 25.9*** | 194.5 ± 25.7*** |
| 27 | 545.0 ± 41.1 | 296.3 ± 30.1***  | 280.0 ± 36.1*** | 252.7 ± 34.4*** |

[a]Mean volume (mm³) of 10 animals ± standard deviation.
[b]Difference not significant relative to vehicle treatment group.
**0.001 < p ≤ 0.01 relative to vehicle treatment group
***p ≤ 0.001 relative to vehicle treatment group This demonstrates that the compounds of the present invention are useful in reducing rates of tumor growth.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences*, 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention, alone, or optionally in combination with an oncolytic, cytotoxic agent, or therapeutic agent, are usually administered in the form of pharmaceutical formulations which may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.01 to about 10 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

For example, one formation may include a compound of Formula I and 2.223 µL of 1N NaOH per mg of compound, with 1% HEC/0.25% Tween 80/0.05% Antifoam 1510-US vehicle according to the following calculation: mL of vehicle to add=(mg of compound/Theoretical mg/mL)−(mg of compound/1200 mg/mL estimated compound density)−mL of 1N NaOH added. Another formulation may include 5% vitamin E-TPGS, 1% hydroxyethylcellulose, and 0.05% Dow Corning Antifoam in purified water.

The bioavailability of compounds of the present invention may be measured by methods known to the skilled artisan. For example a compound of Formula I is administered to Sprague Dawley rats at doses of 1 mg/kg (IV) or 10 mg/kg (oral gavage) in a conventional formulation. An oral formulation may include a suspension (0.25% PS80, 1% HEC, 0.05% Antifoam in water) using milled compound of Formula I. Plasma samples are obtained and concentrations of the compound of Formula I are measured. The compound of Example 57 was evaluated in a method substantially similar to that described above and found to have an oral bioavailability of >100%.

I claim:

1. 4-{4-[4-(4-Fluoro-3-trifluoromethyl-phenyl)-1-methyl-1H-imidazol-2-yl]-piperidin-1-yl}-1H-pyrazolo[3,4-d]pyrimidine, or a pharmaceutically acceptable salt thereof.

2. 4-{4-[4-(4-Fluoro-3-trifluoromethyl-phenyl)-1-methyl-1H-imidazol-2-yl]-piperidin-1-yl}-1H-pyrazolo[3,4-d]pyrimidine p-toluenesulfonate.

3. Crystalline 4-{4-[4-(4-fluoro-3-trifluoromethyl-phenyl)-1-methyl-1H-imidazol-2-yl]-piperidin-1-yl}-1H-pyrazolo[3,4-d]pyrimidine p-toluenesulfonate.

* * * * *